US012616575B2

(12) United States Patent
Gifford, III et al.

(10) Patent No.: US 12,616,575 B2
(45) Date of Patent: May 5, 2026

(54) LEAFLET EXTENSION FOR CARDIAC VALVE LEAFLET

(71) Applicant: Medtronic, Inc., Minneapolis, MN (US)

(72) Inventors: Hanson S. Gifford, III, Woodside, CA (US); Matthew McLean, San Francisco, CA (US); Gaurav Krishnamurthy, Mountain View, CA (US)

(73) Assignee: MEDTRONIC, INC., Minneapolis, MN (US)

( * ) Notice: Subject to any disclaimer, the term of this patent is extended or adjusted under 35 U.S.C. 154(b) by 1200 days.

(21) Appl. No.: 17/294,247

(22) PCT Filed: Nov. 14, 2018

(86) PCT No.: PCT/US2018/061126
§ 371 (c)(1),
(2) Date: May 14, 2021

(87) PCT Pub. No.: WO2020/101676
PCT Pub. Date: May 22, 2020

(65) Prior Publication Data
US 2022/0000621 A1     Jan. 6, 2022

(51) Int. Cl.
*A61F 2/24* (2006.01)

(52) U.S. Cl.
CPC .... *A61F 2/2463* (2013.01); *A61F 2210/0014* (2013.01); *A61F 2220/0033* (2013.01);
(Continued)

(58) Field of Classification Search
CPC .......... A61F 2/24; A61F 2/246; A61F 2/2463; A61B 2017/00584; A61B 17/083
See application file for complete search history.

(56) References Cited

U.S. PATENT DOCUMENTS

| | | | |
|---|---|---|---|
| 6,869,444 B2 | 3/2005 | Gabbay | |
| 7,160,322 B2 | 1/2007 | Gabbay | |

(Continued)

FOREIGN PATENT DOCUMENTS

| | | | |
|---|---|---|---|
| CN | 103079498 A | 5/2013 | |
| EP | 2819618 A1 | 1/2015 | |

(Continued)

OTHER PUBLICATIONS

PCT Search Report and Written Opinion, Appl. No. PCT/US2018/061126, dated Jul. 9, 2019, 12 pages.
(Continued)

*Primary Examiner* — Sarah W Aleman
(74) *Attorney, Agent, or Firm* — Wentsler LLC

(57) ABSTRACT

Leaflet extension devices for cardiac valve leaflets and methods of treating cardiac valve leaflets. Several embodiments are devices for resolving regurgitation in a cardiac valve comprising an expandable member and a cover. The expandable member has a stabilizing portion, a fixation member in opposition to the stabilizing portion, and a coaptation portion between the stabilizing portion and the expandable member. The stabilizing portion and the fixation member clamps the first native leaflet between the stabilizing portion and the fixation member. The coaptation portion projects from the stabilizing portion and the fixation member inwardly with respect to a first native leaflet of a cardiac valve such that the coaptation portion functionally extends the first native leaflet. The cover is attached to at least the coaptation portion of the expandable member.

33 Claims, 31 Drawing Sheets

(52) U.S. Cl.
CPC ................. *A61F 2230/0017* (2013.01); *A61F 2250/0003* (2013.01)

(56) References Cited

U.S. PATENT DOCUMENTS

| | | | |
|---|---|---|---|
| 9,011,523 B2 | 4/2015 | Sequin | |
| 9,592,118 B2 | 3/2017 | Khairkhahan et al. | |
| 9,592,121 B1 | 3/2017 | Khairkhahan | |
| 9,610,163 B2 | 4/2017 | Khairkhahan et al. | |
| 9,907,652 B2 | 3/2018 | Chau et al. | |
| 10,123,874 B2 | 11/2018 | Khairkhahan et al. | |
| 10,166,098 B2 | 1/2019 | Khairkhahan et al. | |
| 10,390,714 B2 | 8/2019 | Wolinsky et al. | |
| 10,449,046 B2 | 10/2019 | Rafiee | |
| 10,470,883 B2 | 11/2019 | Khairkhahan et al. | |
| 10,478,303 B2 | 11/2019 | Khairkhahan | |
| 10,500,048 B2 | 12/2019 | Khairkhahan et al. | |
| 10,512,542 B2 | 12/2019 | Khairkhahan et al. | |
| 10,702,386 B2 | 7/2020 | Khairkhahan et al. | |
| 11,000,372 B2 | 5/2021 | Khairkhahan et al. | |
| 11,083,572 B2 * | 8/2021 | McLean .................. | A61F 2/246 |
| 11,344,410 B2 | 5/2022 | Hacohen et al. | |
| 2003/0199975 A1 | 10/2003 | Gabbay | |
| 2004/0093060 A1 | 5/2004 | Seguin et al. | |
| 2004/0127982 A1 | 7/2004 | Machold et al. | |
| 2005/0010287 A1 | 1/2005 | Macoviak et al. | |
| 2007/0038297 A1 | 2/2007 | Bobo, Jr. et al. | |
| 2008/0077235 A1 | 3/2008 | Kirson | |
| 2010/0217382 A1 | 8/2010 | Chau et al. | |
| 2010/0262233 A1 | 10/2010 | He | |
| 2010/0280604 A1 | 11/2010 | Zipory et al. | |
| 2010/0298929 A1 | 11/2010 | Thornton et al. | |
| 2011/0029072 A1 | 2/2011 | Gabbay | |
| 2011/0276130 A1 | 11/2011 | Alameddine | |
| 2012/0197388 A1 | 8/2012 | Khairkhahan et al. | |
| 2012/0197392 A1 | 8/2012 | DuMontelle et al. | |
| 2013/0006352 A1 | 1/2013 | Yaron | |
| 2014/0067048 A1 | 3/2014 | Chau et al. | |
| 2014/0067054 A1 * | 3/2014 | Chau .................... | A61F 2/2454 623/2.36 |
| 2014/0358223 A1 | 12/2014 | Rafiee et al. | |
| 2015/0119981 A1 | 4/2015 | Khairkhahan et al. | |
| 2015/0142104 A1 | 5/2015 | Braido | |
| 2015/0148893 A1 | 5/2015 | Braido et al. | |
| 2015/0230919 A1 | 8/2015 | Chau et al. | |
| 2015/0327996 A1 | 11/2015 | Fahim et al. | |
| 2015/0366666 A1 * | 12/2015 | Khairkhahan ........ | A61F 2/2466 623/2.11 |
| 2016/0030176 A1 | 2/2016 | Mohl et al. | |
| 2016/0045165 A1 | 2/2016 | Braido et al. | |
| 2016/0045316 A1 | 2/2016 | Braido et al. | |
| 2016/0074164 A1 | 3/2016 | Naor | |
| 2016/0331523 A1 * | 11/2016 | Chau .................... | A61F 2/2466 |
| 2017/0056176 A1 | 3/2017 | Rowe et al. | |
| 2017/0065418 A1 | 3/2017 | Skarsgard | |
| 2017/0095332 A1 | 4/2017 | Bruchman | |
| 2017/0165067 A1 | 6/2017 | Barajas-Torres et al. | |
| 2017/0258589 A1 | 9/2017 | Pham et al. | |
| 2017/0296706 A1 | 10/2017 | Simon et al. | |
| 2017/0319333 A1 | 11/2017 | Tegels et al. | |
| 2018/0143087 A1 | 5/2018 | Gouko et al. | |
| 2018/0147054 A1 | 5/2018 | Chau et al. | |
| 2018/0243087 A1 | 8/2018 | Kapadia | |
| 2018/0271651 A1 | 9/2018 | Christianson et al. | |
| 2018/0325666 A1 | 11/2018 | Ma | |
| 2019/0091047 A1 | 3/2019 | Walsh | |
| 2019/0201191 A1 | 7/2019 | McLean et al. | |
| 2020/0188108 A1 | 6/2020 | Grimm et al. | |
| 2020/0205978 A1 | 7/2020 | Padala et al. | |
| 2020/0222185 A1 | 7/2020 | Kappetein et al. | |
| 2020/0268512 A1 | 8/2020 | Mohl | |
| 2020/0289265 A1 | 9/2020 | Gifford, III et al. | |
| 2020/0360138 A1 | 11/2020 | Ma | |
| 2021/0085462 A1 | 3/2021 | Gifford, III et al. | |
| 2021/0307901 A1 | 10/2021 | Rannani | |
| 2022/0000621 A1 | 1/2022 | Gifford, III et al. | |
| 2022/0039951 A1 | 2/2022 | Khairkhahan et al. | |
| 2022/0125579 A1 | 4/2022 | McLean et al. | |
| 2022/0125586 A1 | 4/2022 | Rafiee | |
| 2022/0160508 A1 | 5/2022 | Miyashiro et al. | |
| 2023/0040083 A1 | 2/2023 | Gifford, III et al. | |

FOREIGN PATENT DOCUMENTS

| | | | |
|---|---|---|---|
| EP | 2918248 A1 | 9/2015 | |
| EP | 3167846 A1 | 5/2017 | |
| JP | 2005535384 A | 11/2005 | |
| WO | 2004014258 A1 | 2/2004 | |
| WO | 2005002424 A3 | 1/2005 | |
| WO | 2012177942 A2 | 12/2012 | |
| WO | 2014189974 A1 | 11/2014 | |
| WO | 2014195422 A1 | 12/2014 | |
| WO | 2014207575 A1 | 12/2014 | |
| WO | 2015052570 A1 | 4/2015 | |
| WO | 2016178136 A1 | 11/2016 | |
| WO | 2017096157 A1 | 6/2017 | |
| WO | 2018142186 A1 | 8/2018 | |
| WO | 2019045910 A1 | 3/2019 | |
| WO | 2020101676 A1 | 5/2020 | |
| WO | 2021027588 A1 | 2/2021 | |
| WO | 2021113449 A1 | 6/2021 | |

OTHER PUBLICATIONS

First examination report for IN Application No. 202117026236 mailed Jan. 20, 2023, 6 pages with English Translation.

Office Action for Japanese Application No. 2021-526692 mailed Nov. 11, 2022, 7 pages with English translation.

Office Action for Japanese Application No. 2021-526692 mailed Jul. 20, 2023, 4 pages with English translation.

First Office Action for EP Application No. 18 815 871.1-1113 mailed Oct. 26, 2023, 7 pages.

Decision of Grant received for Japanese Application No. 2021-526692 mailed Jan. 11, 2024.

First Office Action for Chinese Application No. 201880100627.0 mailed Feb. 2, 2024, 6 pages.

Decision of Grant for Chinese Application No. 201880100627.0 mailed Jun. 12, 2024, 5 pages with English translation.

Intention to Grant received for EP Application No. 18 815 871.1-1113 mailed Jul. 5, 2024, 7 pages.

Examination Report received for Australian Application No. 2018449153 mailed Jul. 26, 2024, 3 pages.

* cited by examiner

Chordae

600C

104

600D

Chordae

LEAFLET EXTENSION FOR CARDIAC VALVE LEAFLET

CROSS-REFERENCE TO RELATED APPLICATIONS

The present application is a 35 U.S.C. 371 U.S. National Phase application of International Application No. PCT/US2018/061126, filed Nov. 14, 2018, which is incorporated herein by reference in its entirety.

The present technology relates generally to implants for repairing a regurgitant or incompetent cardiac valve and for methods of implanting the same. The present technology is particularly useful for repairing a regurgitant mitral valve.

BACKGROUND

Conditions affecting the proper functioning of the mitral valve include, for example, mitral valve regurgitation, mitral valve prolapse and mitral valve stenosis. Mitral valve regurgitation is a disorder of the heart in which the leaflets of the mitral valve fail to coapt into apposition at peak contraction pressures, resulting in abnormal leaking of blood from the left ventricle into the left atrium. There are several structural factors that may affect the proper closure of the mitral valve leaflets. For example, many patients suffering from heart disease have an enlarged mitral annulus caused by dilation of heart muscle. Enlargement of the mitral annulus makes it difficult for the leaflets to coapt during systole. A stretch or tear in the chordae tendineae, the tendons connecting the papillary muscles to the inferior side of the mitral valve leaflets, may also affect proper closure of the mitral annulus. A ruptured chordae tendineae, for example, may cause a valve leaflet to prolapse into the left atrium due to inadequate tension on the leaflet. Abnormal backflow can also occur when the functioning of the papillary muscles is compromised, for example, due to ischemia. As the left ventricle contracts during systole, the affected papillary muscles do not contract sufficiently to effect proper closure.

Mitral valve prolapse, or when the mitral leaflets bulge abnormally up in to the left atrium, causes irregular behavior of the mitral valve and may also lead to mitral valve regurgitation. Normal functioning of the mitral valve may also be affected by mitral valve stenosis, or a narrowing of the mitral valve orifice, which causes impedance of filling of the left ventricle in diastole.

Mitral valve regurgitation is often treated using diuretics and/or vasodilators to reduce the amount of blood flowing back into the left atrium. Other treatment methods, such as surgical approaches (open and intravascular), have also been used for either the repair or replacement of the valve. For example, typical repair approaches have involved cinching or resecting portions of the dilated annulus.

Cinching of the annulus has been accomplished by the implantation of annular or peri-annular rings which are generally secured to the annulus or surrounding tissue. Other repair procedures have also involved suturing or clipping of the valve leaflets into partial apposition with one another.

Alternatively, more invasive procedures have involved the replacement of the entire valve itself where mechanical valves or biological tissue are implanted into the heart in place of the mitral valve. These invasive procedures are conventionally done through large open thoracotomies and are thus very painful, have significant morbidity, and require long recovery periods.

However, with many repair and replacement procedures, the durability of the devices or improper sizing of annuloplasty rings or replacement valves may result in additional problems for the patient. Moreover, many of the repair procedures are highly dependent upon the skill of the cardiac surgeon where poorly or inaccurately placed sutures may affect the success of procedures.

Compared to other cardiac valves, portions of the mitral valve annulus have limited radial support from surrounding tissue and the mitral valve has an irregular, unpredictable shape. For example, the inner wall of the mitral valve is bound by only a thin vessel wall separating the mitral valve annulus from the inferior portion of the aortic outflow tract. As a result, significant radial forces on the mitral annulus could lead to collapse of the inferior portion of the aortic tract with potentially fatal consequences.

The chordae tendineae of the left ventricle are often an obstacle in deploying a mitral valve repair device. The maze of chordae in the left ventricle makes navigating and positioning a deployment catheter that much more difficult in mitral valve repair.

Given the difficulties associated with current procedures, there remains the need for simple, effective, and less invasive devices and methods for treating dysfunctional heart valves.

DETAILED DESCRIPTION

The present technology is directed to cardiac valve devices, and in particular devices for treating regurgitant or incompetent cardiac valves. Although many of the applications are described with respect to the mitral valve, the present technology is not limited to mitral valve applications. The devices of the present technology are intended to repair but not replace the entire native valve.

Several embodiments of the present technology functionally extend one or more native leaflets to facilitate coaptation with other leaflets and thereby reduce regurgitation without piercing through the native leaflet. Some embodiments of the present technology are described with respect to the posterior leaflet of the mitral valve and providing an atraumatic coaptation surface for the anterior leaflet. However, the present technology may be also used to functionally extend the anterior leaflet while providing an atraumatic coaptation surface for the posterior leaflet.

Figure 1:
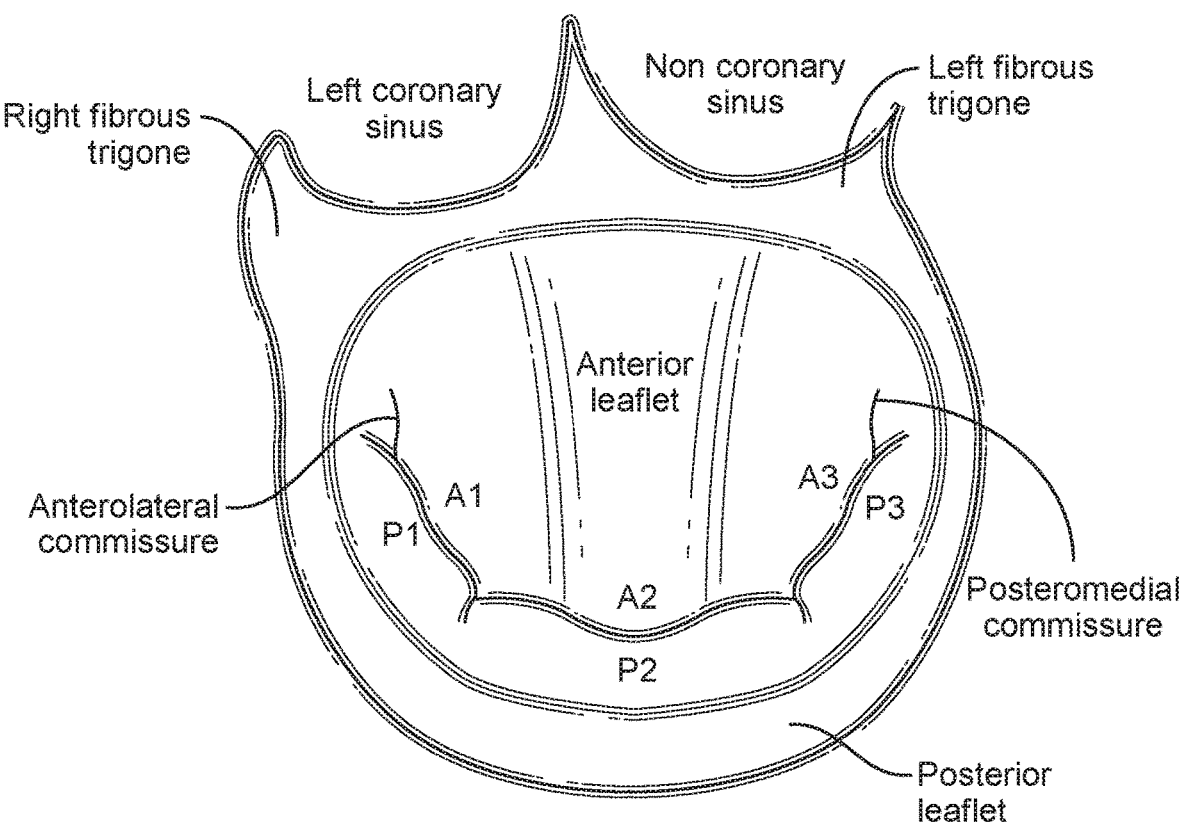
FIG. 1 is a diagram of a native mitral valve.

FIG. 1 shows an example of a mitral valve having an anterior leaflet and a posterior leaflet. The anterior leaflet has a semi-circular shape and attaches to two-fifths of the annular circumference. The motion of the anterior leaflet defines an important boundary between the inflow (diastole) and outflow (systole) tracts of the left ventricle. The posterior leaflet of the mitral valve has a crescent shape and is attached to approximately three-fifths of the annular circumference. The posterior leaflet typically has two well-defined indentations which divide the leaflet into three individual scallops identified as P1 (lateral scallop), P2 (middle scallop), and P3 (medial scallop). The three corresponding segments of the anterior leaflet are identified as A1 (anterior segment), A2 (middle segment), and A3 (posterior segment). The leaflet indentations aid in posterior leaflet opening during diastole.

As shown in FIG. 1, the mitral valve has anterolateral and posteromedial commissures which define a distinct area where the anterior and posterior leaflets come together at their insertion into the annulus. Sometimes the commissures exist as well-defined leaflet segments, but more often this area is a subtle structure, and can be identified using the following two anatomic landmarks: (a) the axis of corresponding papillary muscles, and (b) the commissural chordae, which have a specific fan-like configuration. Several millimeters of valvular tissue separate the free edge of the commissures from the annulus.

The mitral valve is an atrio-ventricular valve, separating the left atrium from the left ventricle. The mitral annulus constitutes the anatomical junction between the left ventricle and the left atrium. The fixed end of the leaflets is attached to the annulus. The anterior portion of the mitral annulus is attached to the fibrous trigones and is generally more developed than the posterior annulus. The right fibrous trigone is a dense junctional area between the mitral valve, tricuspid valve, non-coronary cusp of the aortic annuli, and the membranous septum. The left fibrous trigone is situated at the junction of both left fibrous borders of the aortic and the mitral valve.

The mitral annulus is less well developed at the insertion site of the posterior leaflet. This segment is not attached to any fibrous structures, and the fibrous skeleton in this region is discontinuous. This posterior portion of the annulus is prone to increase its circumference when mitral regurgitation occurs in association with left atrial or left ventricle dilation. The mitral annulus is saddle-shaped, and during systole the commissural areas move proximally, i.e. towards the roof of the atrium, while annular contraction also narrows the circumference. Both processes aid in achieving leaflet coaptation, which may be adversely affected by annular dilatation and calcification. The mitral annulus is surrounded by several important anatomic structures, including the aortic valve, the coronary sinus, and the circumflex artery.

Functional Leaflet Extension

Conventional approaches to addressing annular dilation of the mitral valve have primarily focused on reshaping the annulus using annuloplasty rings or joining the anterior and posterior leaflets to facilitate coaptation. These approaches may not be suitable in situations in which the gap or spacing between the opposing leaflets is too great. Several embodiments of the present technology are leaflet extension devices that functionally extend the native leaflet and attach to the native leaflet, such as without irreversibly disrupting the leaflet (e.g., without piercing into and/or completely through the leaflet), so that the leaflet extension devices can be repositioned and/or removed as needed.

There have also been prior attempts to extend a leaflet. Some conventional approaches utilize an anchoring mechanism which pierces through the leaflet. However, such approaches may be disfavored because they do not allow for repositioning and/or retrieval of the device. Other approaches use a device that extends a leaflet, but existing leaflet extensions are invasively affixed to leaflet by an anchor which pierces through the leaflet.

In contrast, the leaflet extension devices of the present technology non-invasively attach to the leaflet, such as without piercing through the leaflet, to enable repositioning and/or removal of the leaflet extension devices as needed.

Figure 2A:
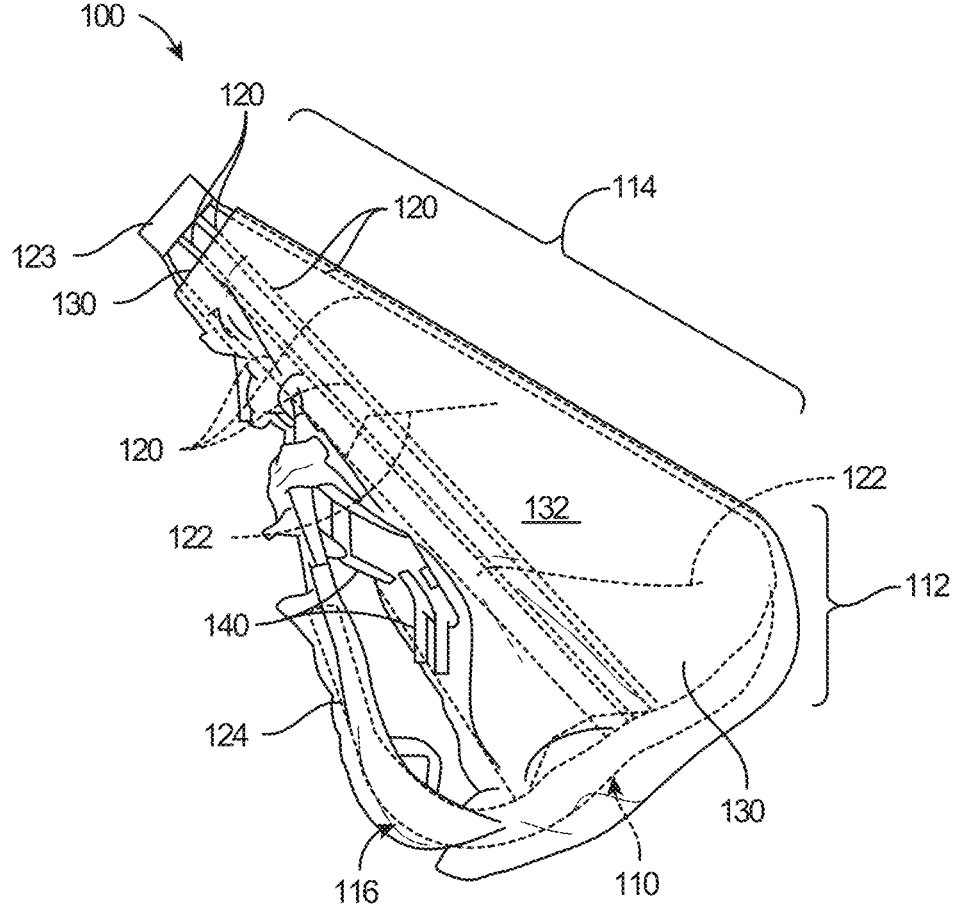
FIGS. 2A-2C illustrate a leaflet extension device configured to be attached to a native cardiac leaflet according to the present technology.
Figure 2B:
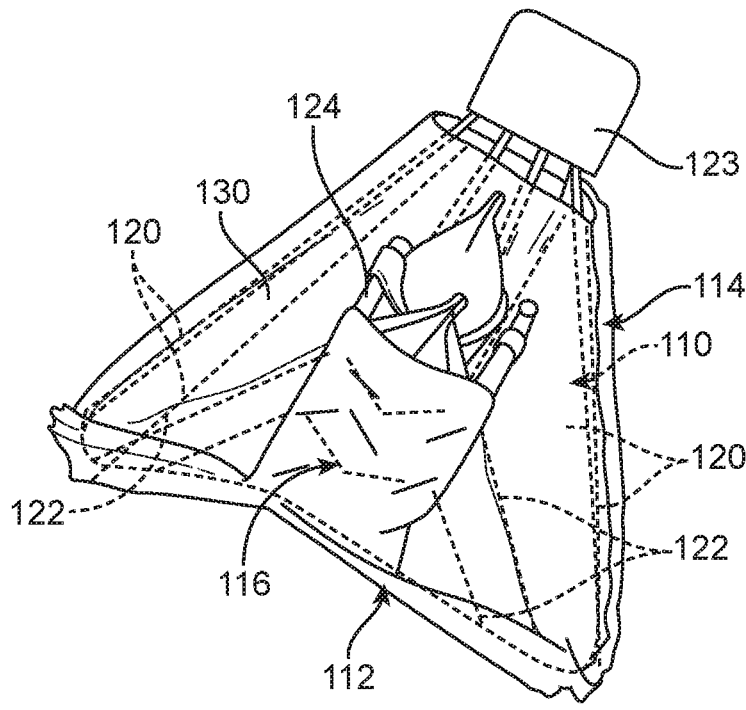
Figure 2C:
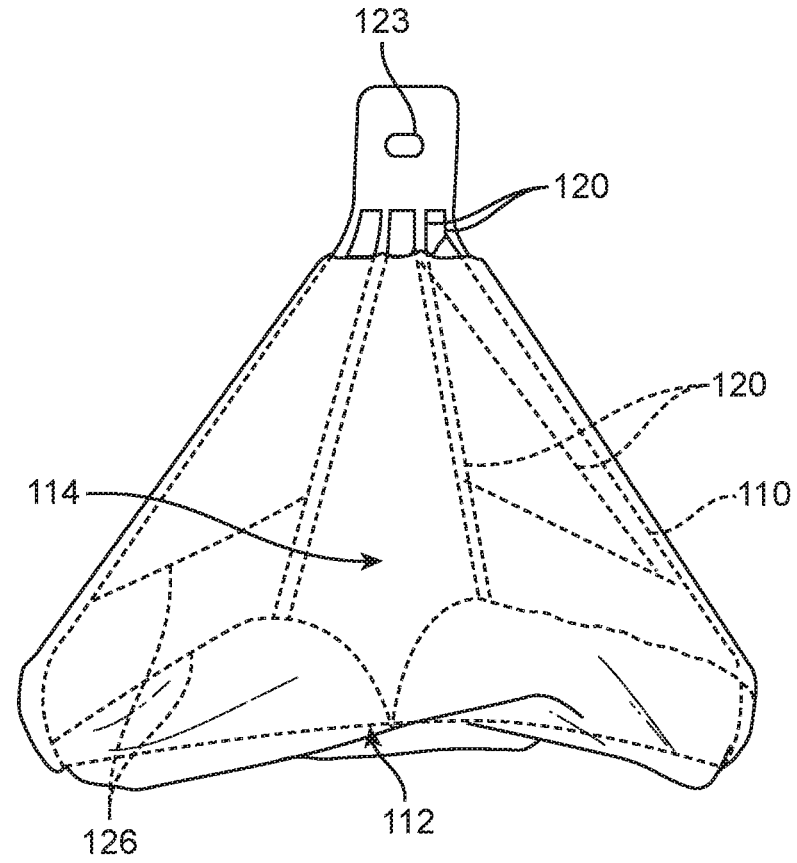

FIGS. 2A-2C depict a leaflet extension device 100 configured for attachment to a native cardiac valve leaflet. In some embodiments, the leaflet extension devices 100 are configured to fill a gap of 3-15 mm between the anterior and posterior leaflets. Additionally, the leaflet extension devices are configured to be attached to the leaflet without irreversibly disrupting (e.g., permanently damaging) the leaflet. This is expected to enable the leaflet extension devices to be removed and repositioned as needed.

The leaflet extension device 100 is configured to provide a prosthetic coaptation surface in place of one of the valve leaflets (anterior or posterior). For the sake of simplicity, the device 100 will be explained with reference to the posterior leaflet of a mitral valve; however, the device 100 is similarly applicable to the anterior leaflet of the mitral valve and to leaflets other cardiac valves, such as the aortic or tricuspid valves.

The leaflet extension device 100 can comprise an expandable member 110 (shown in phantom in FIGS. 2A-2C) and a cover 130. The device 100 has a coaptation portion 112, a stabilizing portion 114, and a fixation member 116. The expandable member 110 has a delivery configuration suitable for being delivered through the vasculature in a catheter and a deployed configuration. In the deployed configuration, the coaptation portion 112 is positioned to provide a prosthetic coaptation surface for one or more native valve leaflets, and the stabilizing portion 114 and the fixation member 116 in combination are configured to secure the device 100 with respect to the valve anatomy. The cover 130 can be attached to or integral with the expandable member 110.

The expandable member 110 may be a frame having a mesh material, a lattice-work frame, and/or one or more struts, or the expandable member may include an inflatable component (e.g., a bladder/balloon) in addition to or in lieu of the frame. In the illustrated example the expandable member 110 comprises a frame having primary struts 120 (shown in phantom) and cross-struts 122 (shown in phantom). The primary struts 120 can be joined at a first end 123 and extend to a second end 124 at the terminus of the fixation member 116. The primary struts 120 can be configured to fan out from the first end 123 and bend in a region that defines the coaptation portion 112 in the deployed configuration.

Figure 3:
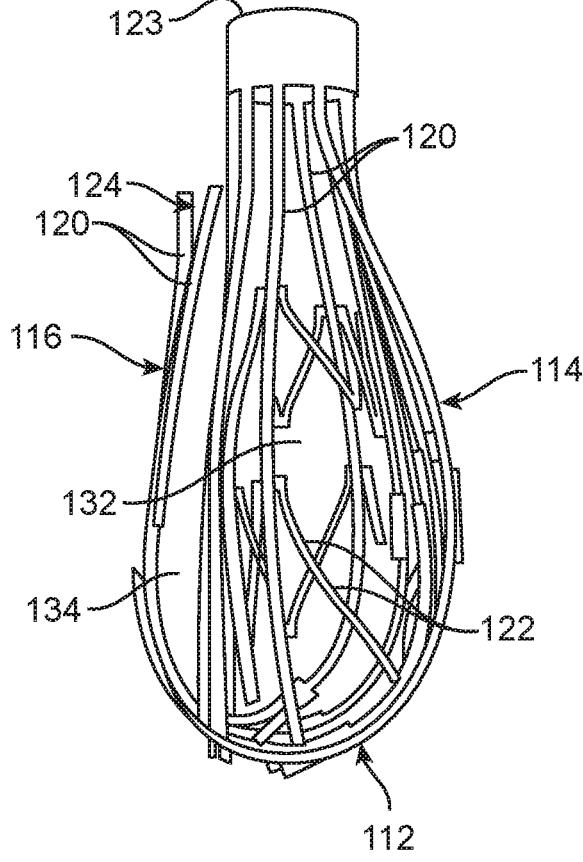
FIG. 3 is a side view of a frame-type expandable member according to the present technology.

FIG. 3 is a side view of a frame-type expandable member 110 without the cover 130. The primary struts 120 can extend and fan out from a hub at the first end 123 to form an interior volume 132 within the coaptation portion 112 and the stabilizing portion 114. The primary struts 120, for example, can bend along the transition from the stabilizing portion 114 and through the coaptation portion 112, and then all or a subset of the primary struts 120 can bend further from the coaptation portion 112 to define at least a portion of the fixation member 116. The fixation member 116 can be a clip that, in the expanded configuration, contacts the stabilizing portion 114 to exert a tight clipping force on the native leaflet. The fixation member 116 can alternatively be separated from the stabilizing portion 114 by a gap 134 as shown in FIG. 3. The cross-struts 122 can be configured to position the primary struts 120 so that the primary struts 120 retain the desired configuration after deployment.

In some of the examples depicted in FIGS. 2A-3, the coaptation portion 112, stabilizing portion 114 and fixation member 116 are integrally formed together. For example, the coaptation portion 112, stabilizing portion 114 and fixation member 116 can be integrally formed by continuous primary struts 120 or cross-struts 122 of the expandable member 110. In other examples, at least one of the coaptation portion 112, the stabilizing portion 114 and/or the fixation member 116 can be a separate component from the others, or each of the coaptation portion 112, stabilizing portion 114 and fixation member 116 can be separate from each other.

Referring to FIGS. 2A-2C, the coaptation portion 112 is intended to extend beyond the free end of the leaflet thereby providing a prosthetic coaptation surface that functionally extends the native cardiac valve leaflet. The coaptation portion 112 may have any smooth shape that mates with the opposing leaflet. The illustrated coaptation portion 112 in FIGS. 2A-2C is a closed loop or ring, but the technology is not limited to the illustrated examples as smooth shapes in general may be used. The coaptation portion 112 and the stabilizing portion 114 enclose the hollow interior volume 132 (FIG. 2A and FIG. 3), which is sealed by the cover 130. After implantation, the hollow volume 132 of the device 100 at least partially fills with blood, which will clot and be replaced by tissue over time. This may contribute to long-term fixation of the leaflet extension device 100. The coaptation portion 112 in combination with the cover 130 provides an atraumatic coaptation surface for the opposing (anterior) native leaflet.

When the expandable member 110 is a frame, it can include struts and/or a mesh formed of any biocompatible material, such as plastic, stainless steel or a super-elastic self-expanding material such a nickel-titanium alloy, e.g., Nitinol®. The cover 130 may be a biocompatible fabric formed of a polymer or biomaterial (Polyethylene terephthalate (PET), expanded polytetrafluoroethylene (ePTFE), silicone, urethane, pericardium, etc.). The cover 130 may be attached to the struts 120, 122 by sutures, adhesives, sintering, and/or other suitable attachment techniques.

In operation, the fixation member 116 is biased toward the stabilizing portion 114 such that the native leaflet is clamped in the gap 134 between the fixation member 116 and the stabilization portion 114 upon deployment. One aspect of several embodiments of the present technology is that the stabilizing portion 114 and the fixation member (ventricular) 116 clamp onto the native leaflet without piercing the native leaflet. The fixation member 116 may include one or more clips configured to clamp to the atrial and ventricular sides of the leaflet, or the like. In the non-limiting example depicted in FIGS. 2A-2C, the fixation member 116 may be a clip which abuts the ventricular side of the native leaflet while the stabilizing portion 114 abuts the atrial side of the native leaflet, but this arrangement may be reversed if desired. In either case the native leaflet is clamped (e.g., sandwiched) between the stabilizing portion 114 and the fixation member 116. In some examples, the leaflet extension device 100 is affixed to the native leaflet solely by the compressive force of the stabilizing portion 114 and the fixation member 116 without piercing through the native leaflet.

Referring to FIG. 2A, the device 100 may further include frictional elements 140 such as cleats which engage or tent into the leaflet. The frictional elements 140 may extend from the stabilizing portion 114 and/or fixation member 116. For example, or the frictional elements 140 may be attached to or integrally formed with the stabilizing portion 114 and/or the fixation member 116. The frictional elements 140 may be sharpened to facilitate engagement with the leaflet. In some cases, the frictional elements 140 may penetrate into the native cardiac valve leaflet without piercing completely through the native leaflet. In other cases, the frictional elements 140 pierce completely through the full thickness of the native valve leaflet.

The leaflet extension device 100 is intended to be delivered and implanted in a beating heart using a minimally invasive technique. For example, the leaflet extension may be delivered via a catheter using a transfemoral approach. The leaflet extension device 100 is attached to the desired leaflet using the fixation member 116.

The stabilizing portion 114 and/or the fixation member 116 may be sized to engage with all or a portion of the native leaflet. When they engage the entire leaflet they may support a torn leaflet. Alternatively, the stabilizing portion 114 and/or the fixation member 116 may be sized to engage with only a portion of the native leaflet, e.g., central scallop P2 of the posterior leaflet, leaving scallops P1 and P3 mobile. In this example, P1 and P3 are free to coapt with the anterior leaflet (opposing leaflet).

Figure 4:
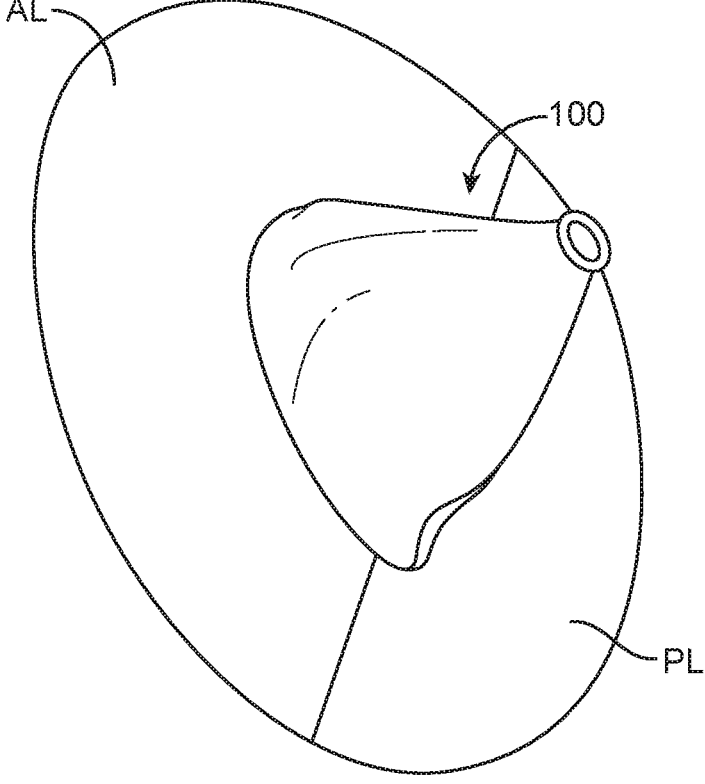
FIG. 4 illustrates a leaflet extension device implanted in a mitral valve according to the present technology.
Figures 5A, 5B:
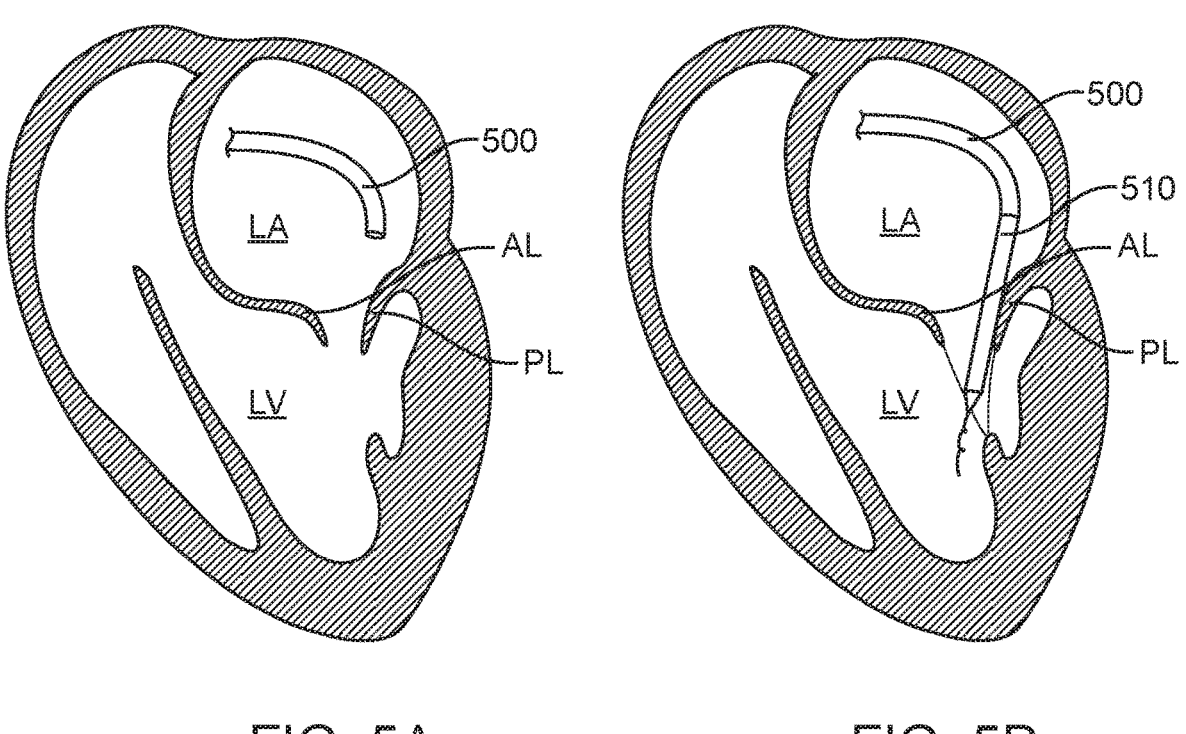
FIGS. 5A-5E depict a method of implanting a leaflet extension device according to the present technology.
Figure 5C:
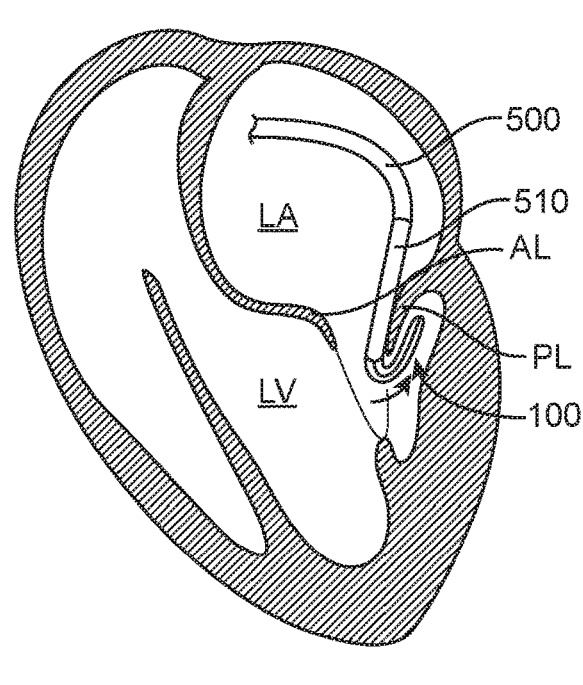
Figure 5D:
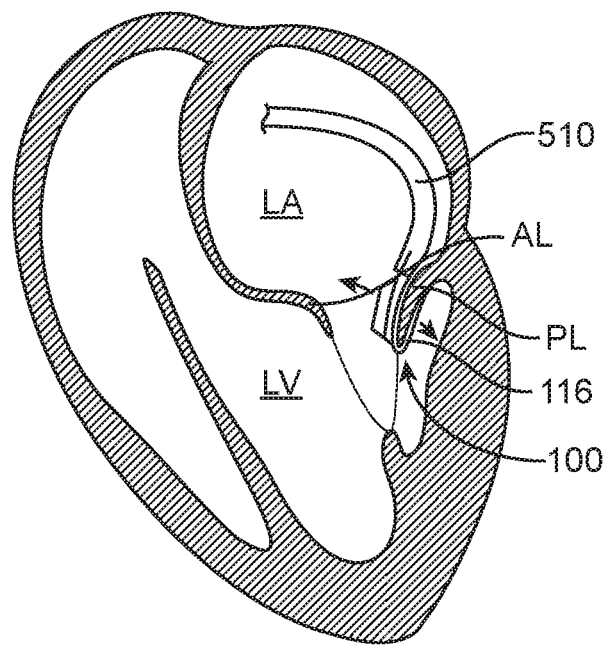
Figure 5E:
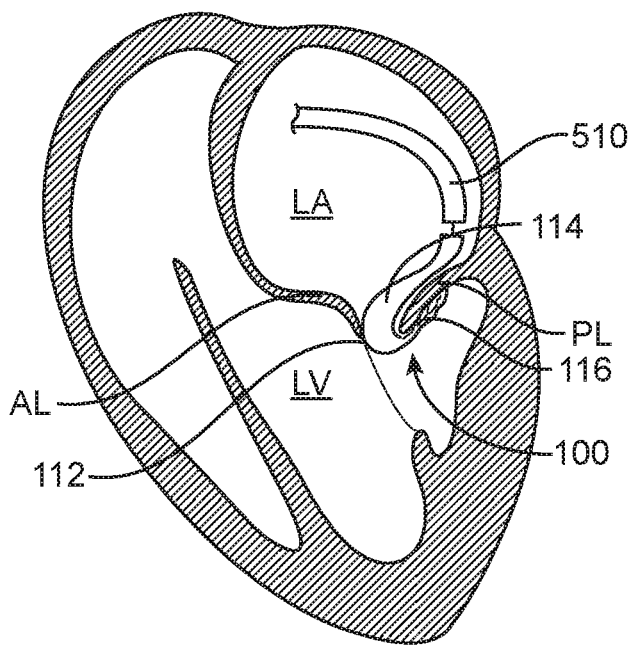

FIG. 4 is an isometric view of the device implanted in a native mitral valve as viewed from the left atrium, and FIGS. 5A-5D illustrate an example of implanting the leaflet extension device 100 at a native mitral valve. The leaflet extension device 100 can be compressed into a tubular sheath for delivery via a trans-septal or trans-atrial access. It could also be delivered via trans-apical access or trans-aortic access. Referring to FIG. 5A, a delivery catheter 500 or sheath can be positioned in the left atrium LA above the P2 portion of the posterior leaflet PL of the mitral valve. A device catheter 510 can then be advanced through the delivery catheter 500 and positioned at the native valve near the middle of the P2 leaflet edge of the posterior leaflet PL while the leaflet extension device 100 (FIGS. 2A-3) is still contained within the device catheter 510, as shown in FIG. 5B. Referring to FIG. 5C, as the fixation member 116 is then partially released from the device catheter 510, the fixation member 116 folds against the ventricular surface of the leaflet. During this process, the physician can confirm that the leaflet extension device 100 is at the appropriate height and that the fixation member 116 passes between the chordae. FIG. 5D shows the process after the fixation member 116 has been fully deployed and stabilizing portion 114 is partially deployed such that the stabilizing member splays medially and laterally. FIG. 5E illustrates the process after the leaflet extension device 100 has been deployed such that the expansion member 110 (FIG. 3) has expanded to the deployed configuration. At this stage of the process, the posterior leaflet PL is clamped between the stabilizing portion 114 and the fixation member 114, while the anterior leaflet A1 coapts against the atraumatic surface of the coaptation portion 112. Once the sheath is retracted to the atrial end of the device 100, the effectiveness of the device in reducing or eliminating mitral regurgitation can be assessed. At this stage the leaflet extension device 100 is functionally deployed but still connected to the delivery catheter. If the device 100 is performing appropriately, it may be detached/disengaged from the delivery catheter. If not, the device catheter 510 and/or the delivery catheter 500 can be re-advanced to linearize and compress the device 100 for removal or repositioning.

Figure 6A:
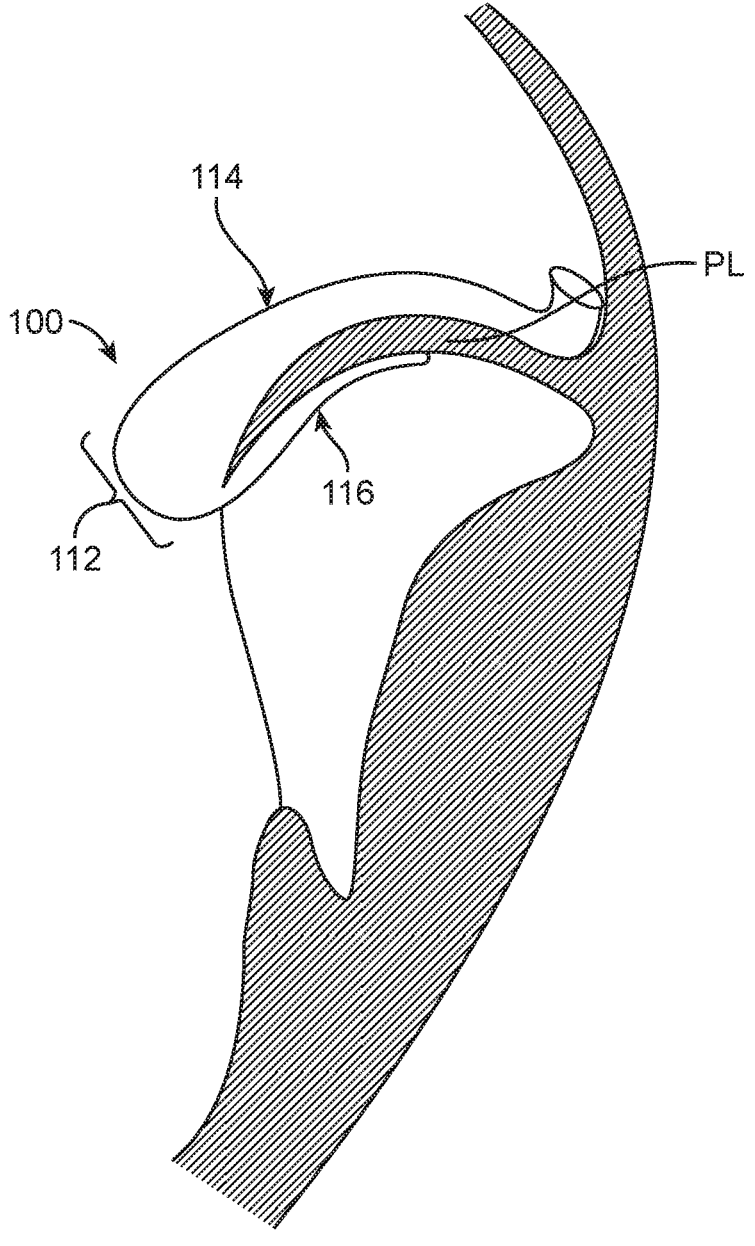
FIGS. 6A-6B depict leaflet extension devices according to the present technology.
Figure 6B:
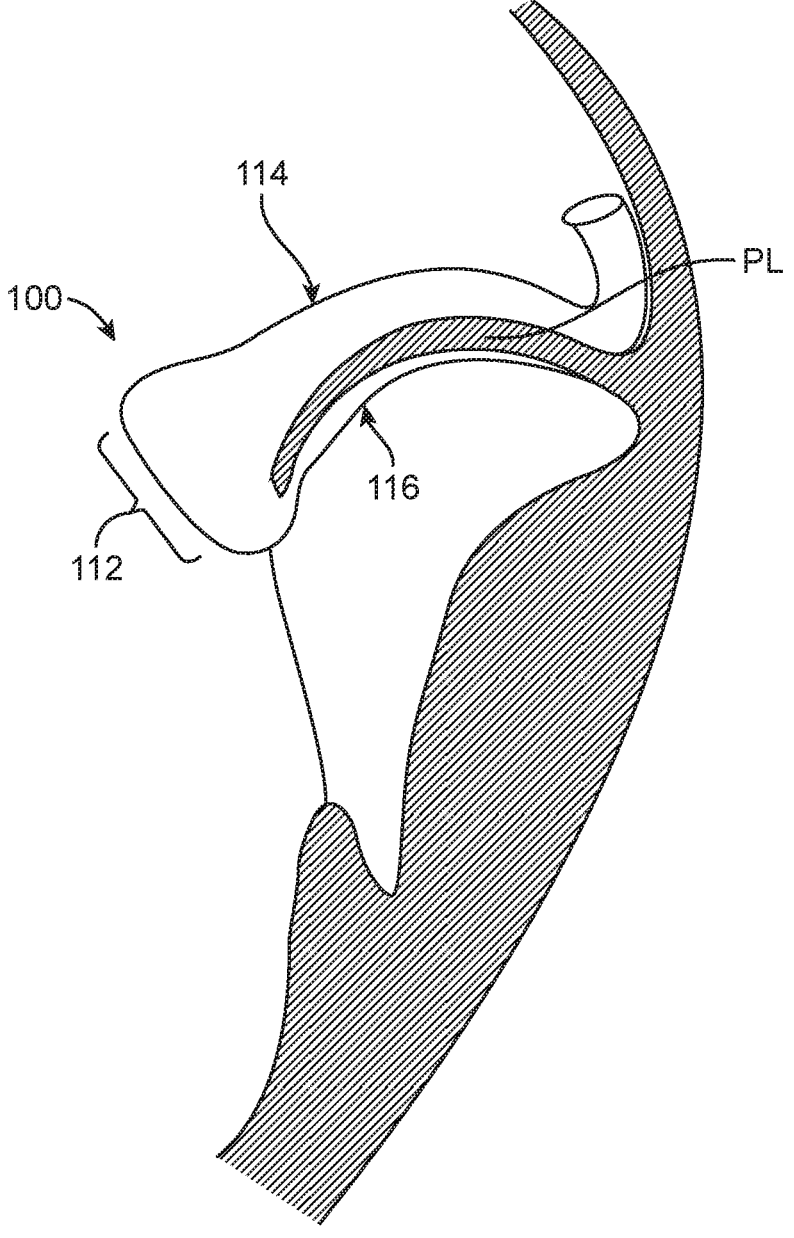

The shape of the leaflet extension device 100 can be configured to enhance its effectiveness in engaging the native posterior leaflet and/or coapting with the native anterior leaflet. FIG. 6A shows the leaflet extension device 100 with the stabilizing portion 114 and/or the fixation member 116 configured such that they hold the posterior leaflet PL in approximately the natural curved shape of the native leaflet. FIG. 6B shows the leaflet extension device 100 with the stabilizing portion 114 and/or the fixation member 116 configured such that they hold the native posterior leaflet PL in a relatively flattened shape. The flattened shape shown in FIG. 6B may position the leading edge of the native leaflet and the chordae tendineae slightly closer to the anterior leaflet (not shown). The coaptation portion 112 may have a somewhat concave shape on the atrial side of the posterior leaflet PL, as seen in FIG. 6B, to position the coaptation surface of the coaptation portion 112 to coapt with the native anterior leaflet. The coaptation portion 112 may have a curved or even round shape as seen in cross-section in FIG. 6A, or a somewhat more linear vertical shape as seen in FIG. 6B, so that the anterior leaflet has a consistent coaptation surface over a range of leaflet heights. The specific shape of the device 100 could be varied to address different anatomical variations between patients, such as partial flail leaflets in patients with degenerative disease, or tethered leaflets in patients with functional mitral disease. The shape could also be varied to accomplish various types of coaptation geometries. The coaptation portion 112 could be relatively vertical. Other options include configurations in which the anterior leaflet can close against the ventricular aspect of the implant in a "trap-door" geometry.

Figure 7A:
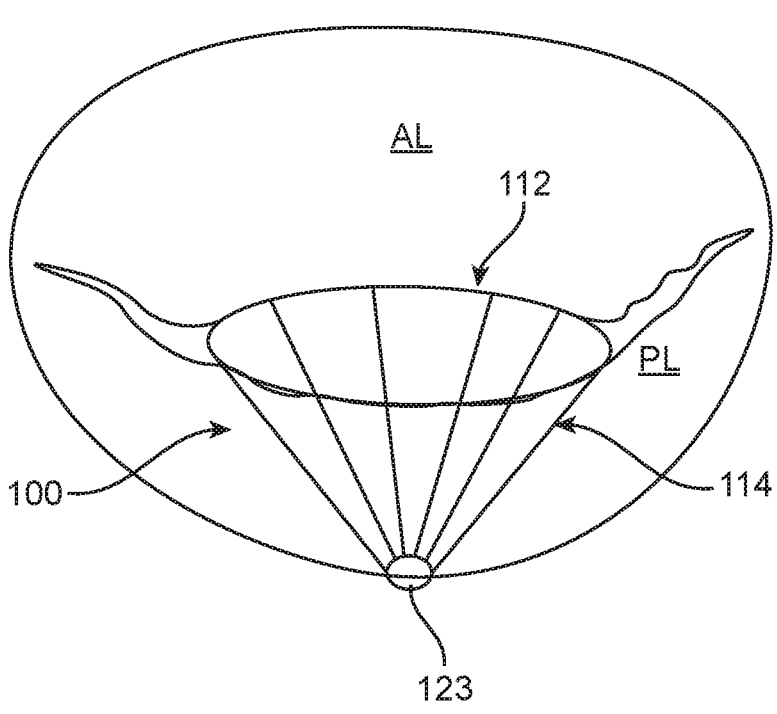
FIGS. 7A-7B depict stabilizing portions of leaflet extension devices according to the present technology.
Figure 7B:
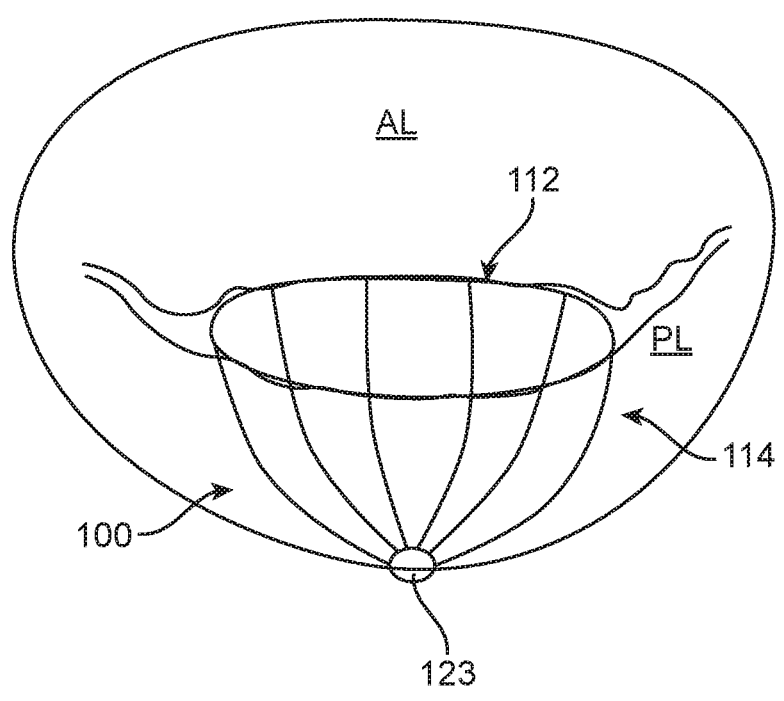

FIGS. 7A and 7B illustrate the leaflet extension device 100 from the left atrium after implantation. The device 100 may extend along approximately 25-35 mm of the posterior leaflet PL edge and follow the curved edge of the posterior leaflet PL. The coaptation portion 112 may curve slightly in the opposite direction as shown in FIG. 7A, or it may be relatively more straight as shown in FIG. 7B.

The length of the native leaflet measured from the annulus to the leaflet edge is in the range of approximately 20-30 mm. The stabilizing portion 114 of the device 100 abuts the atrial surface of the posterior leaflet PL and may be relatively straight, as shown in FIG. 7A, or the stabilizing portion 114 may be bulbous (e.g., splayed) to engage/support as much surface area of the native leaflet as possible as shown in FIG. 7B.

Figures 8A, 8B:
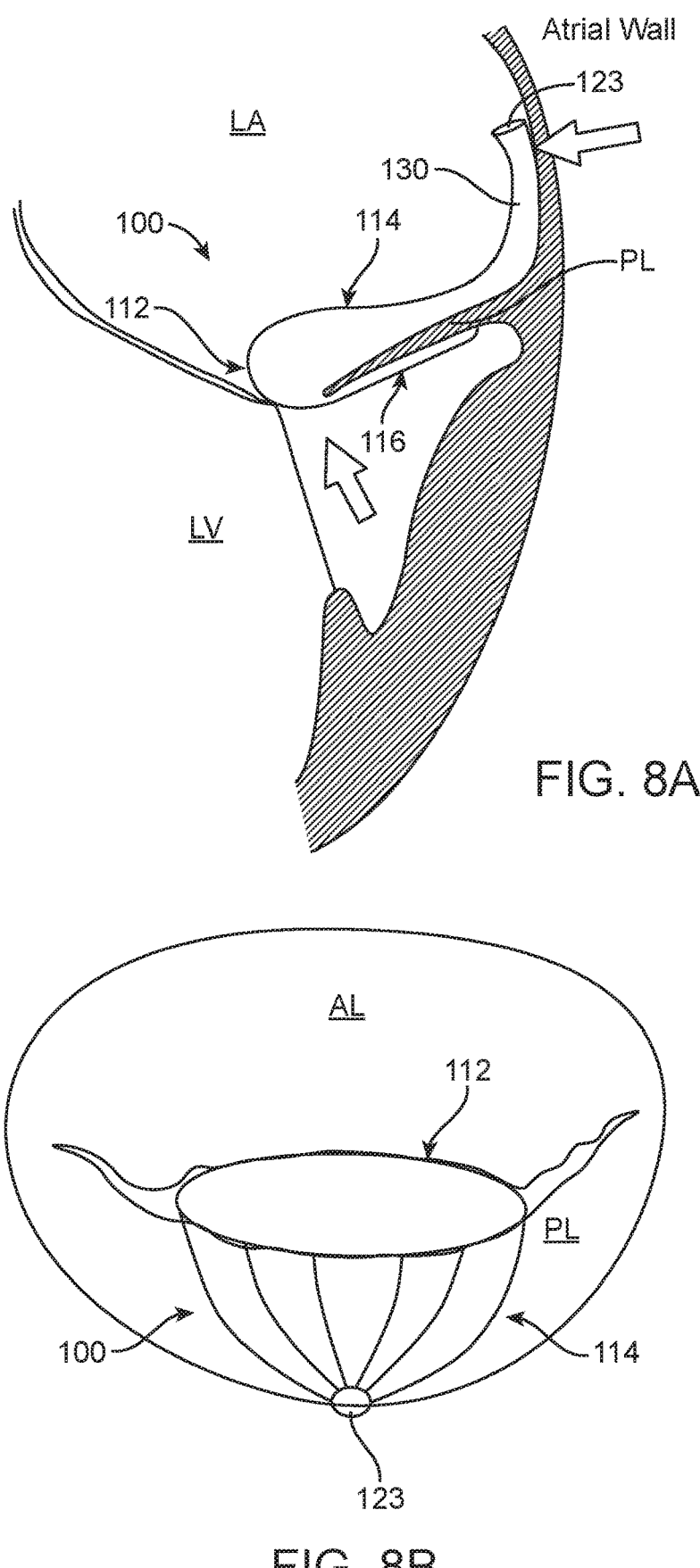
FIGS. 8A-8B depict a leaflet extension device according to the present technology.

The stabilizing portion 114 may extend beyond the fixed end of the leaflet and partially up the atrial wall above the mitral annulus, as shown in FIG. 8A. This configuration of the stabilizing portion 114 increases the longitudinal dimension of the device 100 so that it can readily expand laterally and cover more of the atrial surface to further enhance the stability of the device 100. For example, such a long stabilizing portion 114 may brace the device 100 against the atrial wall to inhibit the device 100 from flipping into the left atrium under systolic blood pressure and can thus facilitate treatment of mitral regurgitation due to posterior leaflet flail or prolapse.

The cover 130 of the device 100 shown in FIG. 8A may promote ingrowth into the atrial wall. This ingrowth may result in the middle scallop P2 of the posterior leaflet assuming the closed position permanently such that the middle scallop P2 would effectively act as a stop. The device 100 may include an anchoring mechanism (not illustrated) such as a screw, tack, an eyelet for a screw or tack, or the like useful for fixing the end of the stabilizing portion 114 to the atrial wall or the mitral annulus.

Figure 9A:
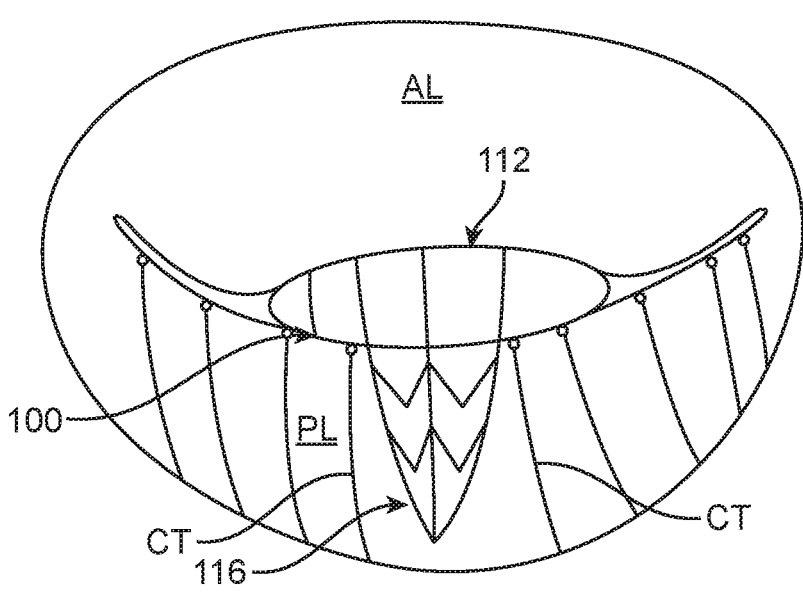
FIGS. 9A-9E depict leaflet extension devices with fixation members that extend between chordae tendineae according to the present technology.

The posterior leaflet of the human mitral valve typically has a gap between the posteromedial and anterolateral groups of chordae, which may be approximately 8-10 mm wide, and the fixation member 116 can be configured to be consistently positioned between the chordae tendineae (CT). FIG. 9A, for example, shows a fixation member 116 of the device 100 configured to lay against the ventricular surface of the native posterior leaflet. The fixation member 116 shown in FIG. 9A has a relatively narrow width and pointed/rounded tip that can be predictably positioned in the gap between the chordae tendineae CT.

Figure 9B:
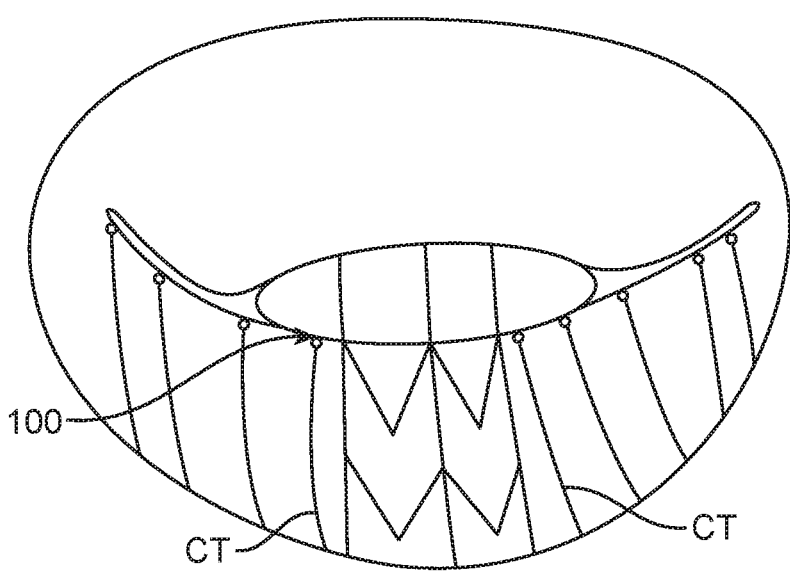
Figure 9C:
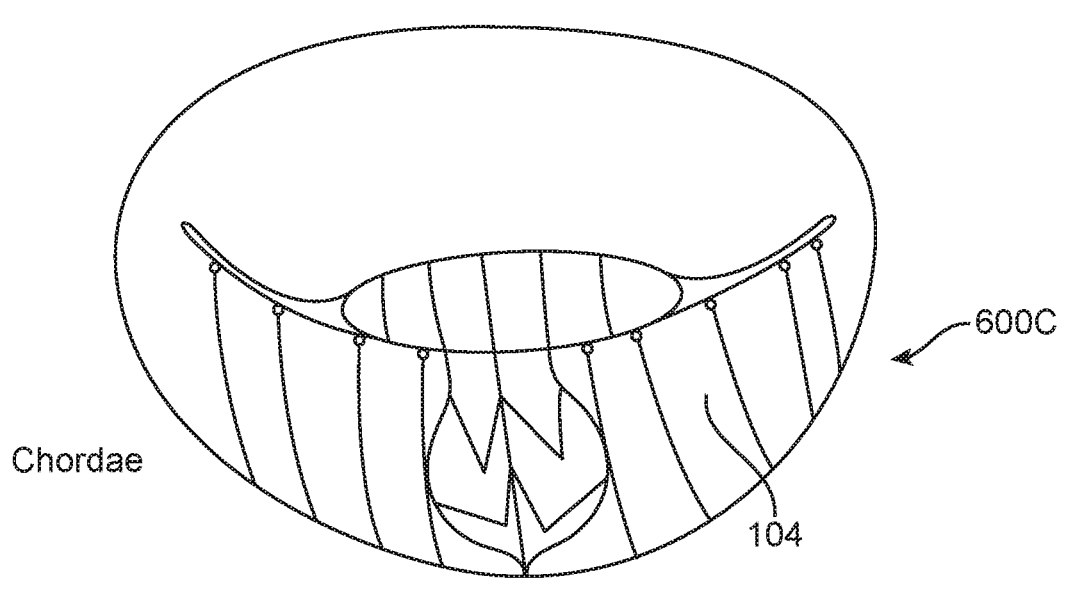
Figure 9D:
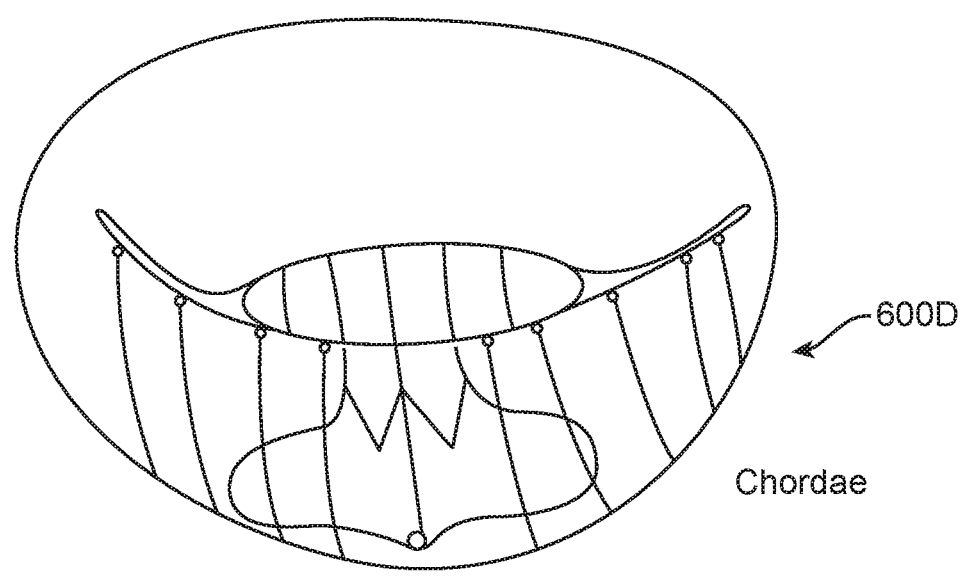

FIGS. 9B-9D show various examples of the fixation member 116 that are linear (FIG. 9B), spade-shaped (FIG. 9C) or splayed-shape (FIG. 9C). The wider fixation members 116 shown in FIGS. 9B-9D may help stabilize the device 100, such as when a portion of the posterior leaflet may be flailing or prolapsing.

Figure 9E:
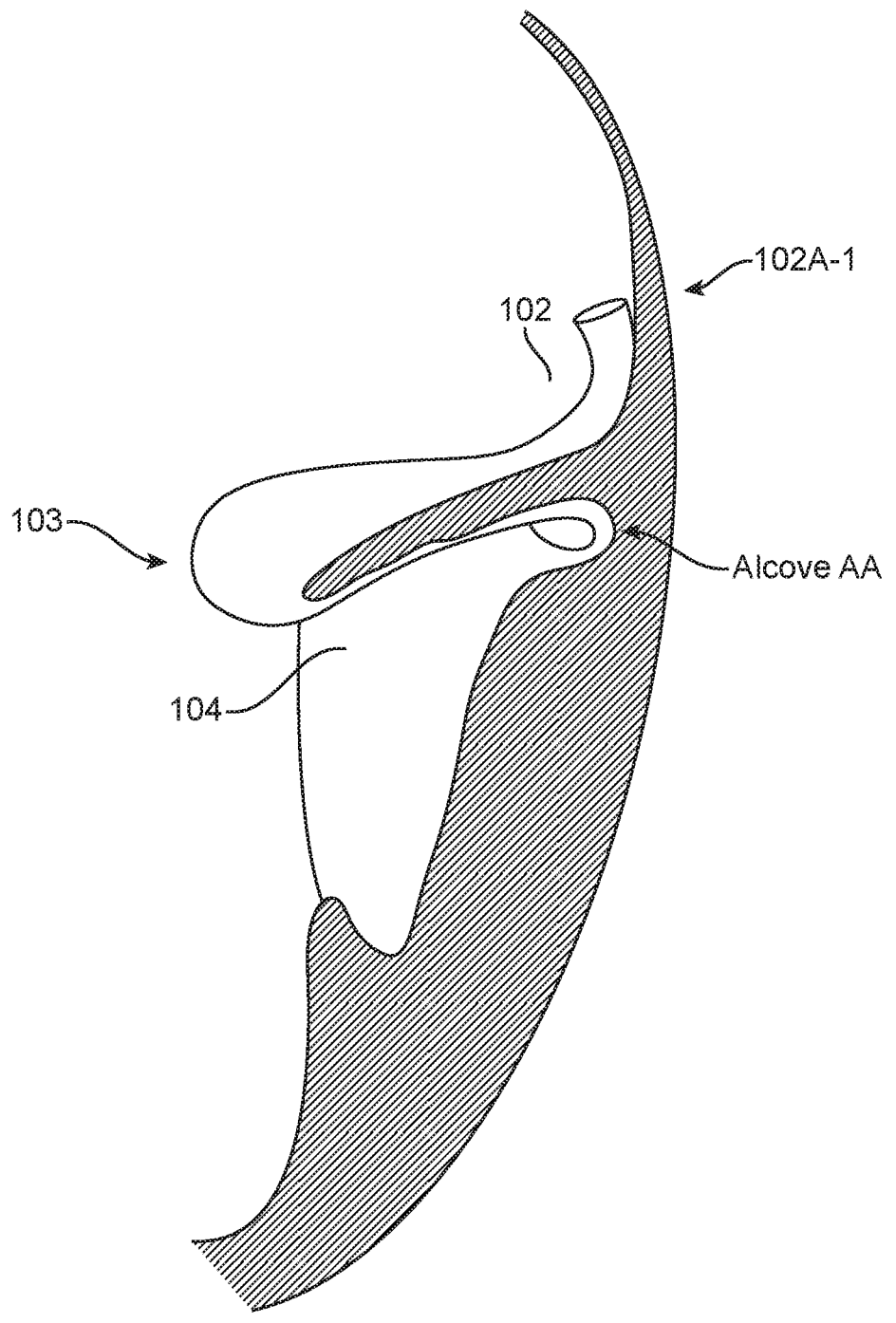

Referring to FIG. 9E, the fixation members 116 may extend into the naturally occurring alcove AA located between the ventricular wall muscle and the posterior leaflet. This extension of the fixation member 116 may enhance the stabilization of the device 100, which is expected to make it easier to form a more secure contact with the native leaflet and to inhibit it from flipping upward under systolic blood pressure.

In some of the previously described embodiments, one or more of the fixation members 116 extend through the gap between the posteromedial and anterolateral groups of chordae and press against the ventricular surface of the posterior leaflet to hold the implant in place. One or more fixation members 116 may also extend under the posterior leaflet more medially and laterally, passing between chordae wherever they conveniently pass. Such embodiments may require that the device 100 be expanded laterally and medially before such fixation members are extended between the chordae to avoid being bunched in the central gap between the chordae. In several applications it is desirable to have the fixation members 116 fold into only the central gap between the medial and lateral groups of chordae to mitigate entangling the fixation member 116 with the chordae.

Figure 10A:
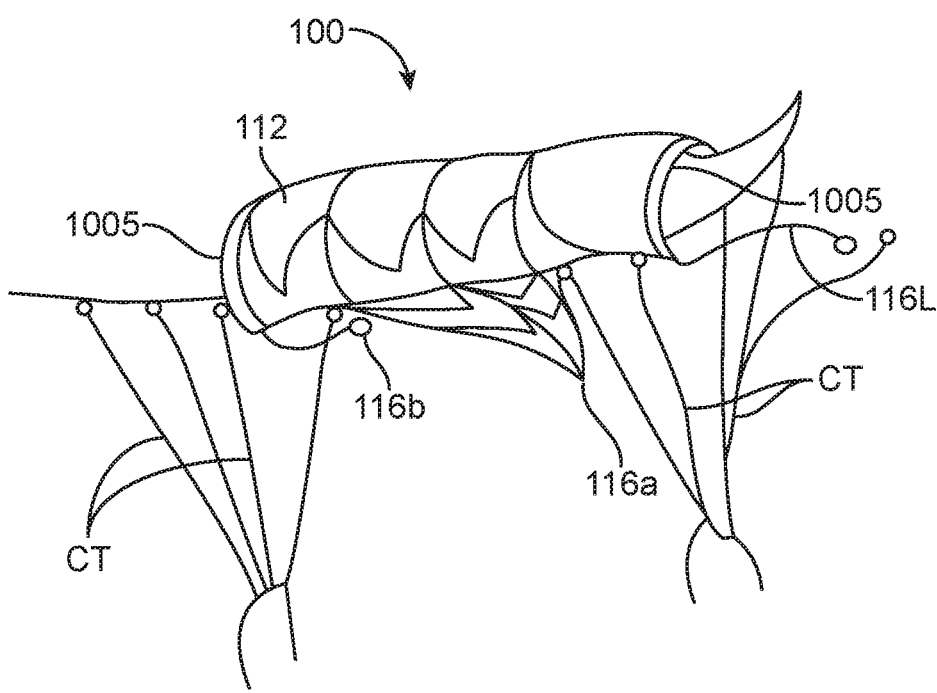
FIGS. 10A-10B depict leaflet extension devices with fixation elements extending between chordae tendineae according to the present technology.

FIG. 10A shows a leaflet extension device 100 having a first fixation member 116a and second fixation members 116b. The first fixation member 116a can be similar to the fixation members 116 described above with respect to FIGS. 2A-9E. The second fixation members 116b are nearer the lateral and medial margins of the device, and in such cases it may be advantageous to deploy the second fixation members 116b or other ventricular elements after initially deploying the device 100. For example, after the device 100 has expanded medially and laterally, the second fixation members 116b can be advanced into gaps between the chordae. In some embodiments, the second fixation members 116b can be advanced through tubes 1005 attached to the lateral and medial portions of the device 100. The tubes 1005 may be formed of polyimide or the like, and they may be attached to the expandable member 110 or the cover 130 of the device 100. For example, the tubes 1005 can be attached to the expandable member 110 at the same time as the cover 130 is attached, such as by sewing all of these elements to each other. It may be desirable to have one or more of the struts of the stabilizing portion 114 (FIGS. 2A-2C) include a lumen sized to accommodate the second fixation members 116b thereby eliminating the need for the tubes 1005.

The second fixation members 116b may be formed of a resilient material such as a super-elastic nickel-titanium alloy, e.g., Nitinol®, pre-formed to follow the shape of the deployed implant so that they are biased to apply pressure to the ventricular surface of the native leaflet. The second fixation members 116b can also include an atraumatic end, such as paddles or loops, that have an increased surface area to maximize their grip strength and mitigate trauma to the native leaflet.

Figure 10B:
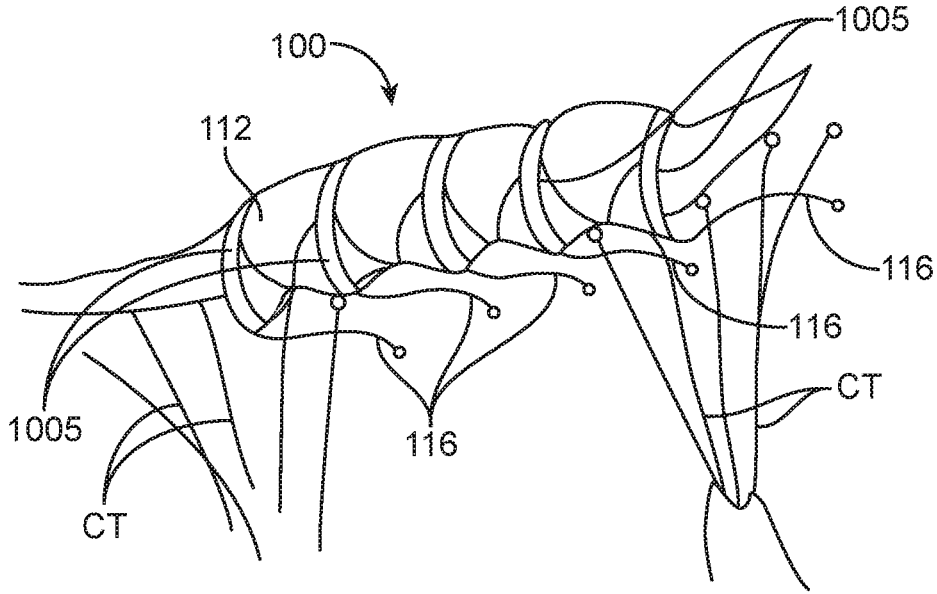

The device 100 may be easier to position in the native valve with fixation members 116 that are not integral continuations of the struts that form the coaptation portion 112. The fixation members 116 can accordingly be separate struts that are advanced individually or together against the ventricular surface of the posterior leaflet. FIG. 10B, for example, shows such a device 100 with fixation members 116 similar to the second fixation members 116b that are advanced through tubes 1005 to be positioned against the ventricular surface of the native leaflet.

Figure 11A:
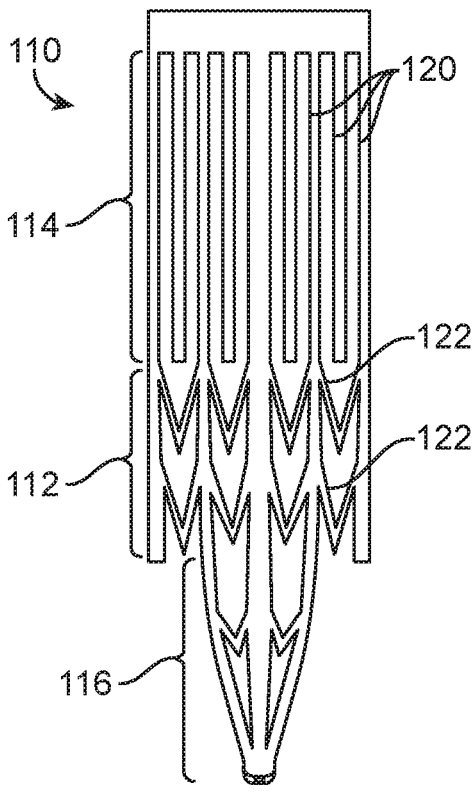
FIGS. 11A and 11B illustrate a leaflet extension device according to the present technology.
Figure 11B:
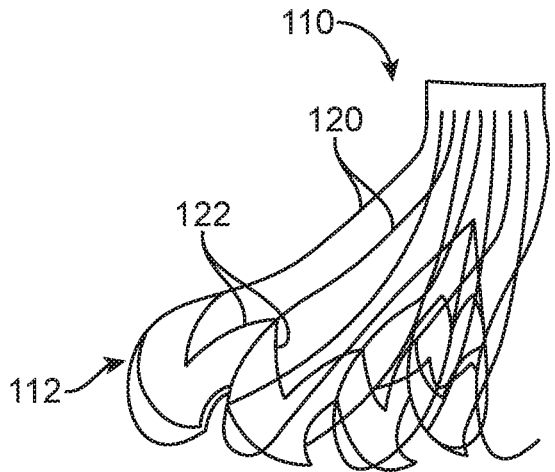

FIGS. 11A and 11B show variations of expandable members 110 suitable for use in the device 100. The expandable member 110 can be cut from a flat sheet of nickel-titanium alloy with numerous primary struts 120 and cross-struts 122. As best shown in FIG. 11A, a number of the central primary struts 120 can extend continuously through the stabilizing portion 114, the coaptation portion 112, and the fixation member 116. The stabilizing portion 114 of the struts 120 can be biased to lay against the atrial surface of the posterior leaflet, and the coaptation portion 112 can be configured to define the support for the prosthetic coaptation surface. The coaptation portion of the primary struts 120 can be supported by the cross-struts 122 to enhance the stability of the device 100. In the example shown in FIGS. 11A-11B, there are four primary struts configured to lay against the atrial surface and five primary struts 120 are configured that define the structure of the coaptation surface 112. The fixation structure 116 is supported by the three central primary struts 120 so that the fixation structure 116 extends under the ventricular surface of the posterior leaflet.

To deliver the device 100 from a femoral venous access site via a trans-septal puncture, the outer diameter of the entire device 100 and delivery system should generally not exceed 24 French (8 mm diameter), although larger diameters may be suitable for some applications. As a result, if the device 100 has nine primary support struts 120 arrayed linearly, each primary support 120 can have a maximum width of 0.5 mm (0.020 inch) as a non-limiting example.

To achieve smaller diameters, the device 100 can be constructed by cutting a cylindrical nickel-titanium alloy tube with a number (perhaps 6-12) of linear elements (e.g., primary struts 120). These linear elements could be connected by cross-struts (e.g., chevrons) or other flexible elements for strength, stability, and enhanced friction against the leaflet surface. Approximately half of the linear elements can define the stabilizing portion 114, which can be configured to follow the atrial surface of the posterior leaflets, and half of the linear elements can define the coaptation portion 112, which can be curved to create the leaflet extension shape.

Figure 12:
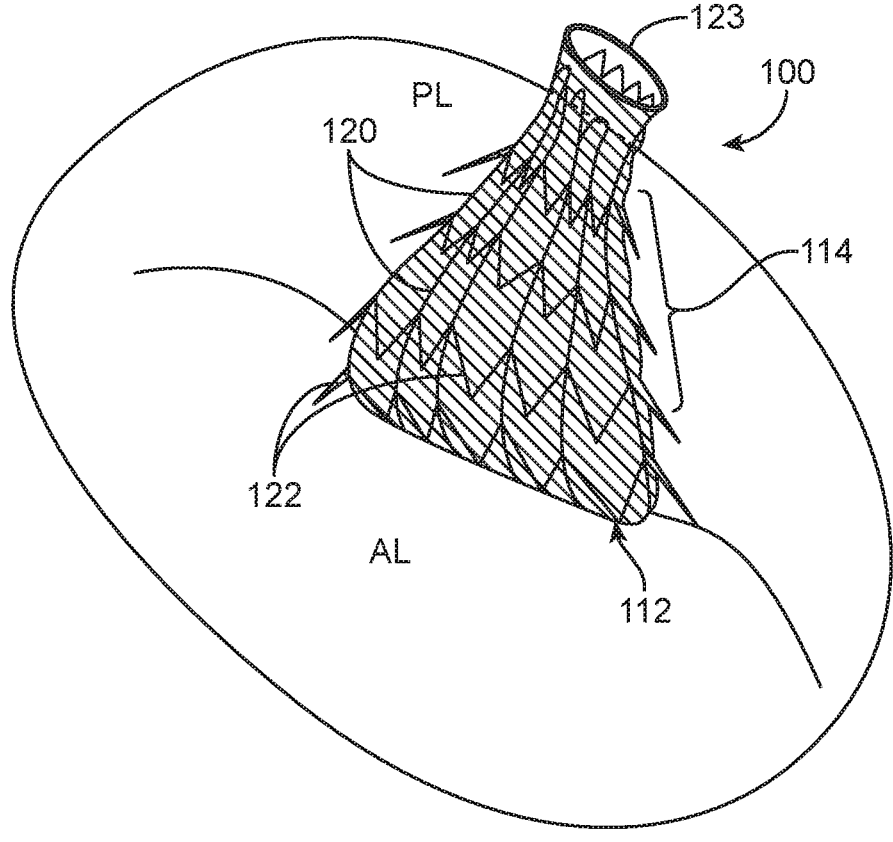
FIG. 12 illustrates a leaflet extension device according to the present technology.

FIG. 12 shows an embodiment of the device 100 having a somewhat flattened shape and cross-struts 122 that project outwardly for enhanced fixation. In such embodiments, the cross-struts 122 at the edges of the device 100 might extend further laterally and medially to further stabilize the device 100. If a portion of the posterior leaflet was flailing or there was a misalignment between the P1-P2 or P2-P3 segments of the native leaflet, such expanded cross-struts 122 may further stabilize and align the leaflet segments.

Figure 13A:
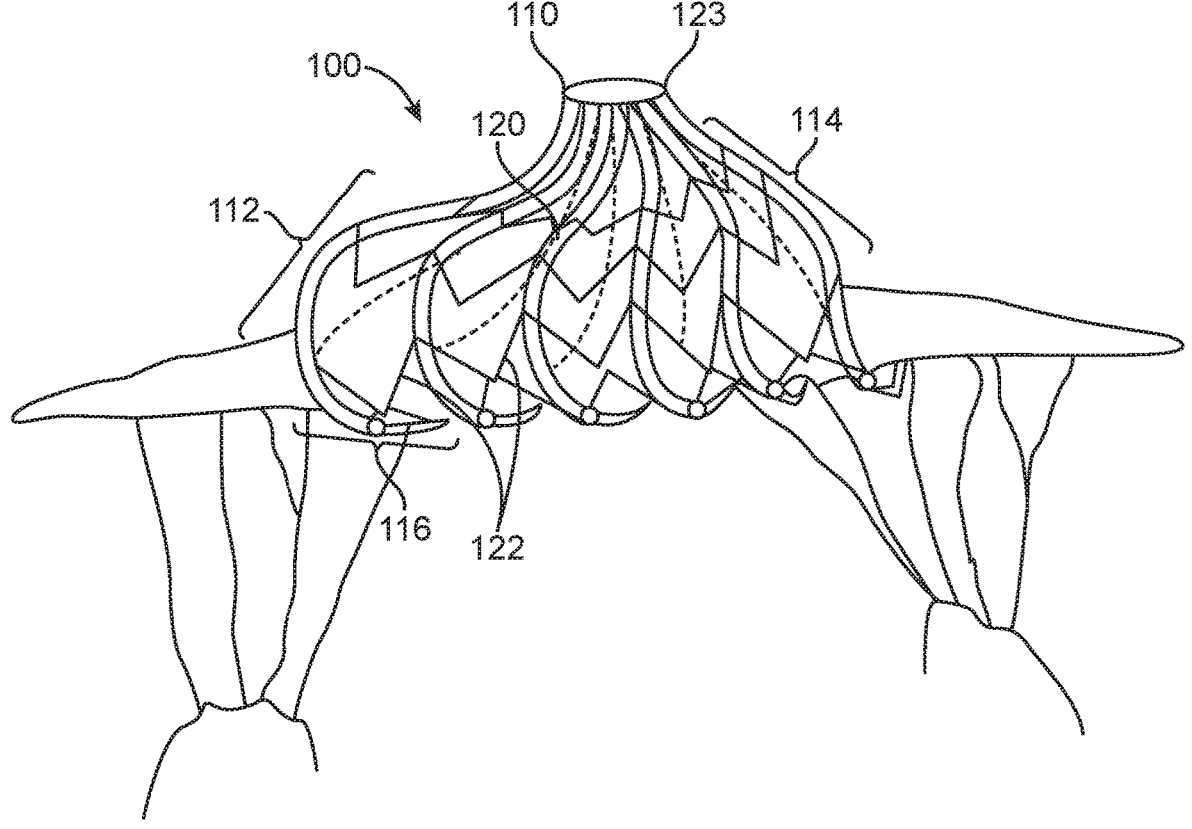
FIGS. 13A-13B depict a leaflet extension device according to the present technology.
Figure 13B:
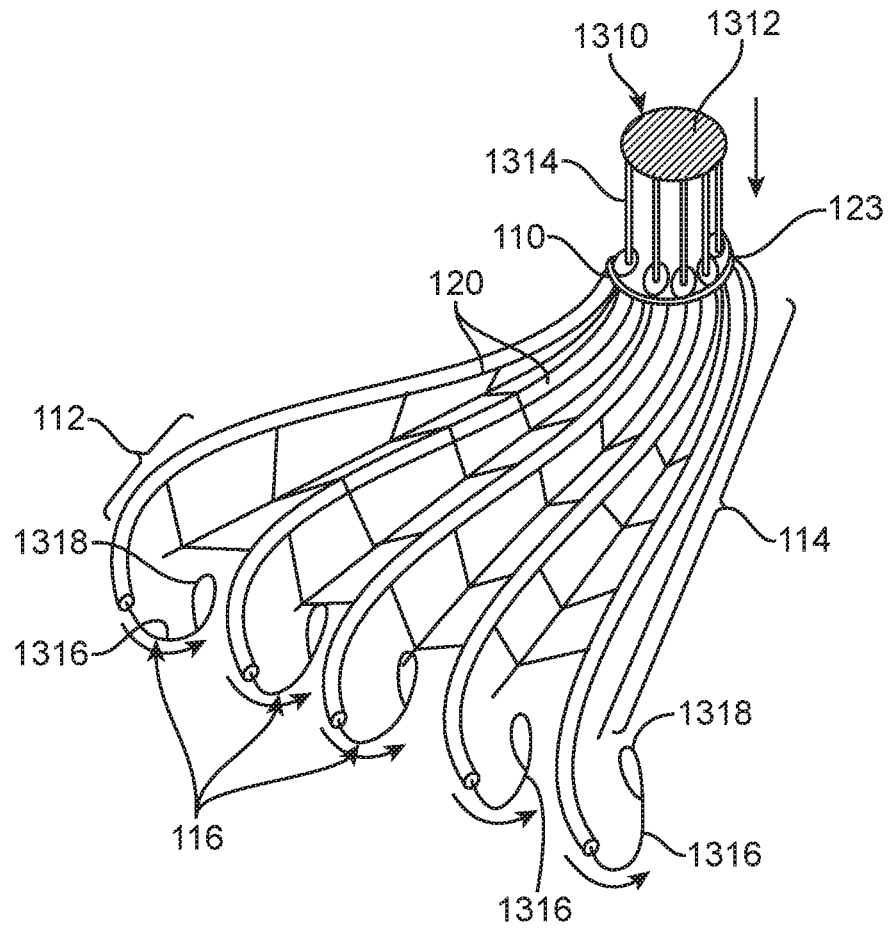

FIGS. 13A and 13B show aspects of the expandable member 110 of the device 100 having individual fixation members 116. The primary struts 120 can extend from the first end 123 and through the stabilizing portion 114 and the coaptation portion 112 such that the primary struts 120 extend to a point underneath the posterior leaflet. The device 100 can have primary struts 120 with lumens though which individual fixation members 116 can be moved from a retracted position to an extended position. As a result, individual fixation members 116 can be extended from the primary struts 120 to engage the ventricular surface of the native leaflet and hold the implant 100 in place. The device 100 in FIG. 13A has independently advanceable fixation members 116 at the lateral and medial edges of the implant 100. Alternatively, all of the fixation members 116 of the device 100 shown in FIG. 13B are independently advanceable. The primary struts 120 may be hollow metal or polymeric tubes. In other embodiments, the devices 100 shown in FIGS. 13A and 13B have solid primary struts 120 and separate tubes, such polyimide tubes, are affixed to the primary struts 120. If such separate tubes are attached to the sides of the primary struts 120 corresponding with the inside diameter of the tubes, then when the implant 100 is compressed for delivery the overall device diameter would be minimized. The coaptation portion 112 can be covered by a fabric covering as described above.

FIG. 13B further illustrates an extension mechanism 1310 for extending/retracting the fixation members 116. The extension mechanism 1310 can include individual wires having a proximal portion 1314, a distal portion 1316, and an atraumatic tip 1318. The distal portions 1316 and the tips 1318 of the wires define the fixation members 116. The proximal portion 1314 of each movable wire may extend proximally to a handle or be releasably attached to a separate push-wire in the delivery system. This would enable the independent movement of each wire into the appropriate position. Alternatively, the extension mechanism 1310 could have a plunger 1312 and one or more of the wires can be attached to the plunger 1312 so that the wires attached to the plunger could all be advanced/retracted simultaneously (as shown in FIG. 13C). This would simplify the structure of the delivery catheter, speed up the implantation process, and simplify the release of the implant from the delivery catheter.

FIGS. 14A-14D show the device 100 having a coaptation portion 112 that is deployed independently with respect to the stabilizing portion 114. For example, the coaptation portion 112 can have separate elements that are deployed by advancing them relative to the elements of the stabilizing portion 114. The coaptation portion 112 could be adjustable so that by further advancing the coaptation portion relative to the stabilizing portion 114, the implant 100 could be expanded to further improve coaptation.

Figure 14A:
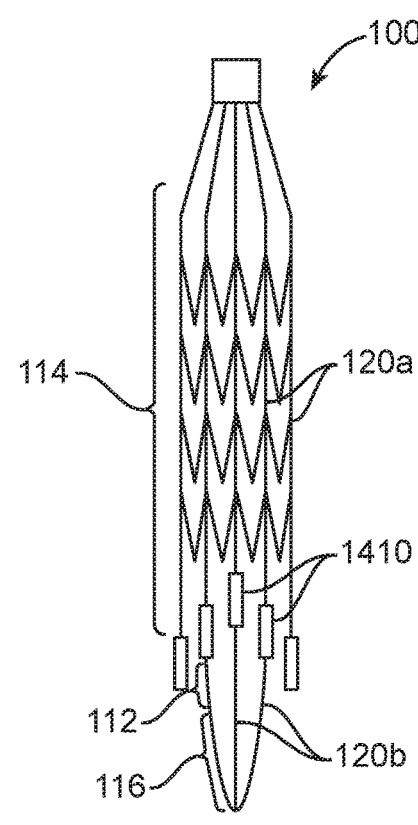
FIGS. 14A-14G depict leaflet extension devices according to the present technology.
Figure 14B:
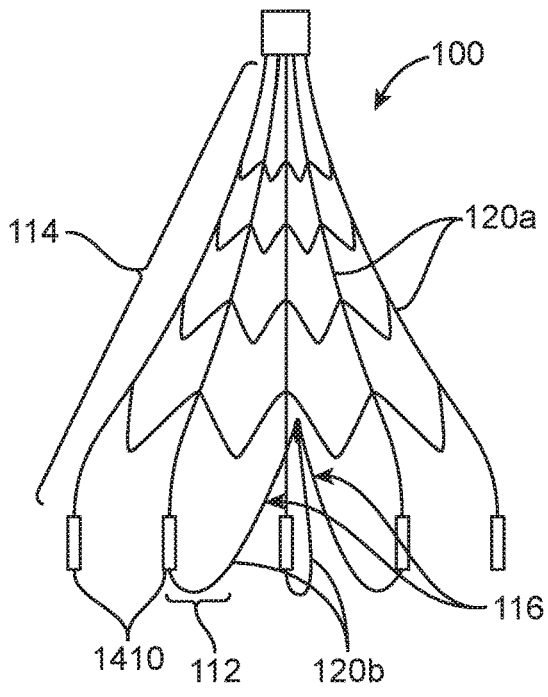

FIGS. 14A and 14B show some embodiments of the device 100 in which the stabilizing portion 114 and coaptation portion 112 are linked at the distal region of the stabilizing portion 114. More specifically, the stabilizing portion 114 has first primary struts 120a and eyelets 1410 at the ends of the first primary struts 120a, and the coaptation portion 112 has second primary struts 120b configured to extend through the eyelets 1410. The devices 100 can further include cross-struts 122 between the first primary struts 120a of the stabilizing portion 114. The first primary struts 120a of the stabilizing portion 114 can be cut from one flat metal sheet (e.g., a shape memory material such as Nitinol), and the second primary struts 120b of the coaptation portion 112 can be cut from a second metal sheet (e.g., a shape memory material such as Nitinol; see, e.g., FIGS. 14A and 14C).

Figure 14C:
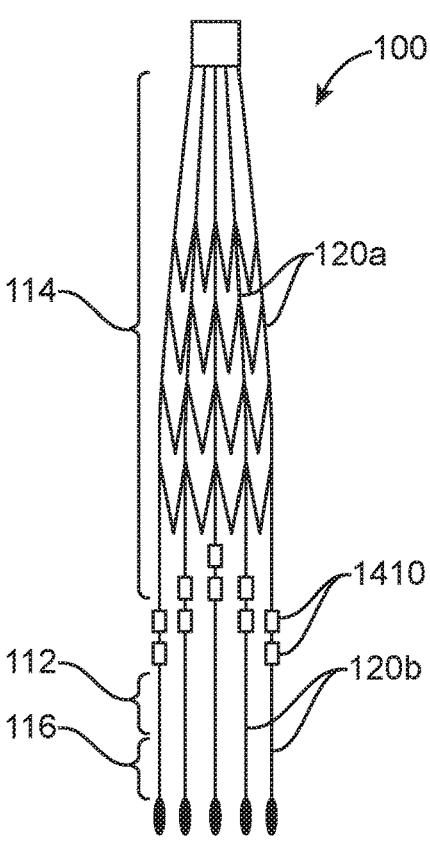
Figure 14D:
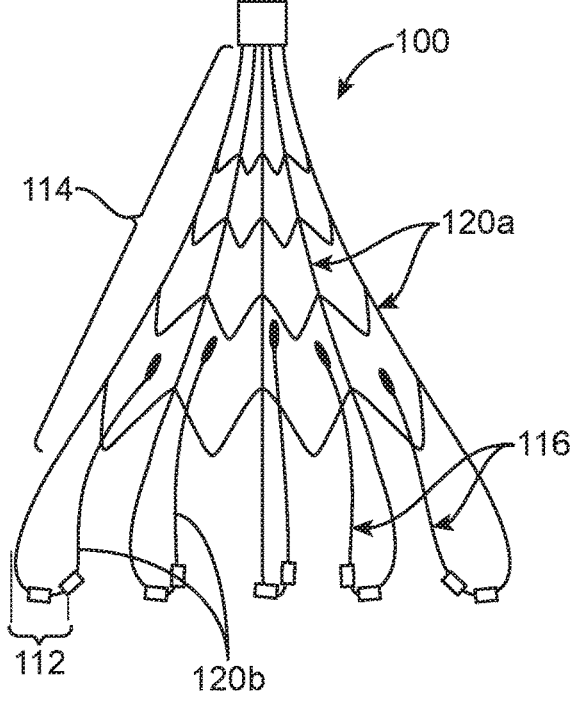

FIGS. 14B and 14D show how the first and second primary struts 120a-b are configured to have curves approximating the desired final shape in the expanded state. The device 100 shown in FIGS. 14A and 14B has central second primary struts 120b that are connected at their distal ends to define a fixation portion 116. The device 100 shown in FIGS. 14C and 14D has separate second primary struts 120b that curve separately from each other to define a plurality of fixation members 116. The second primary struts 120b of the coaptation portion 112 pass through the openings/eyelets 1410 at the distal ends of the first primary struts 120a of the stabilizing portion 114. The first and second primary struts 120a and 120b made may be held together at the proximal end of the device 100.

Once the device 100 is deployed with the stabilizing portion 114 pressing against the surface of the posterior leaflet and splayed laterally and medially, the coaptation portion 112 can be further advanced so that the distal extensions of the of the second primary struts 120b, which define the fixation members 116, fold under against the ventricular surface of the posterior leaflet. This motion clamps the device 100 in place while simultaneously raising the coaptation portion 112 and extending the posterior leaflet towards the anterior leaflet.

Figure 14E:
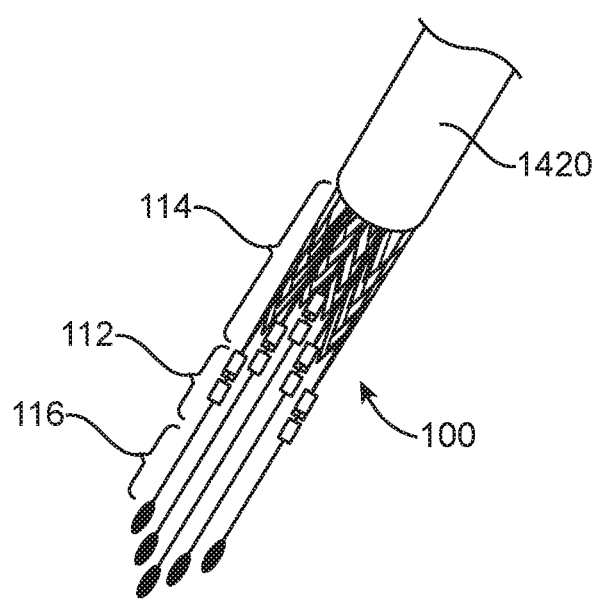
Figure 14F:
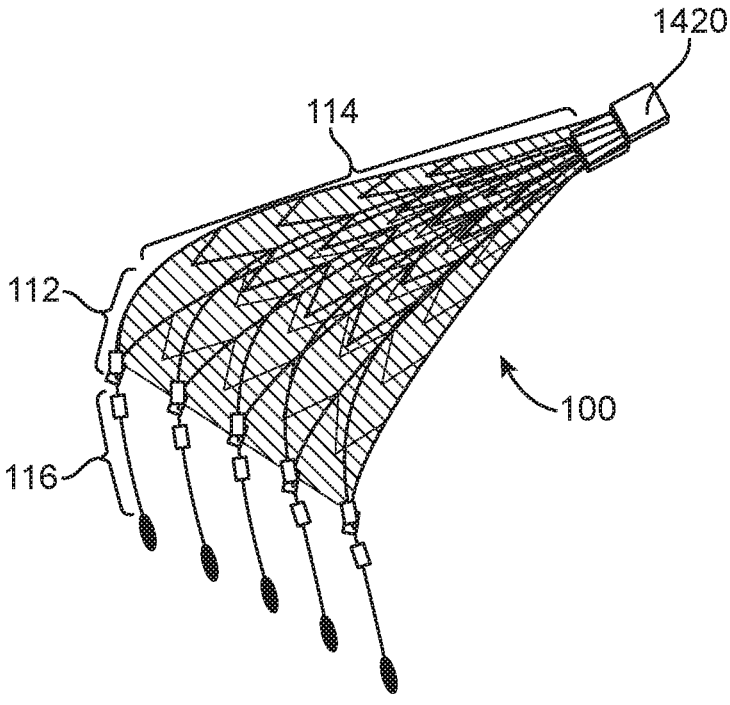
Figure 14G:
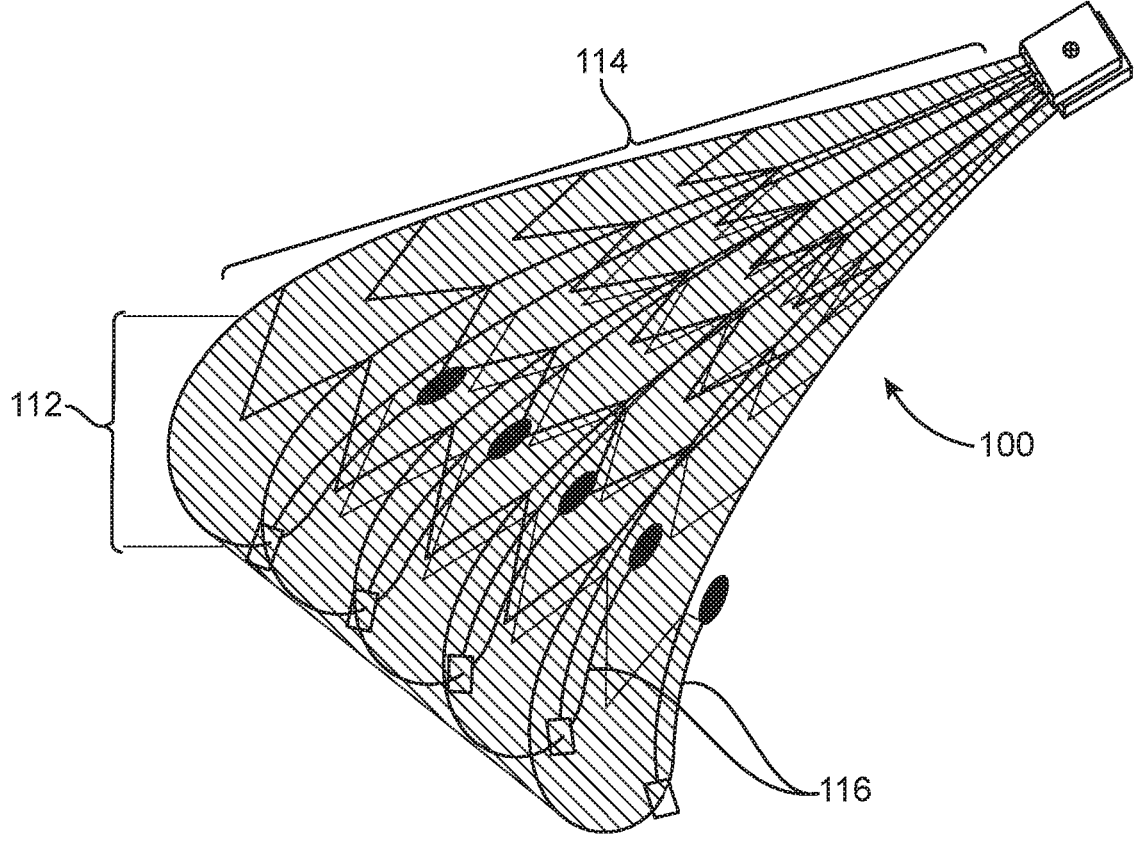

FIGS. 14E-14G show the deployment sequence of the device 100 shown in FIGS. 14C and 14D. FIG. 14E shows the device 100 after it has been partially exposed from the distal portion of a delivery catheter 1420. At this point, the stabilizing portion 114, the coaptation portion 112, and the fixation members 116 can be at least substantially aligned with each other. FIG. 14F shows the device 100 after the coaptation portion 112 begins to bend, and FIG. 14G shows the device 100 after the stabilizing portion 114, the coaptation portion 112 and the fixation members 116 have moved into their deployed shapes.

Figure 15A:
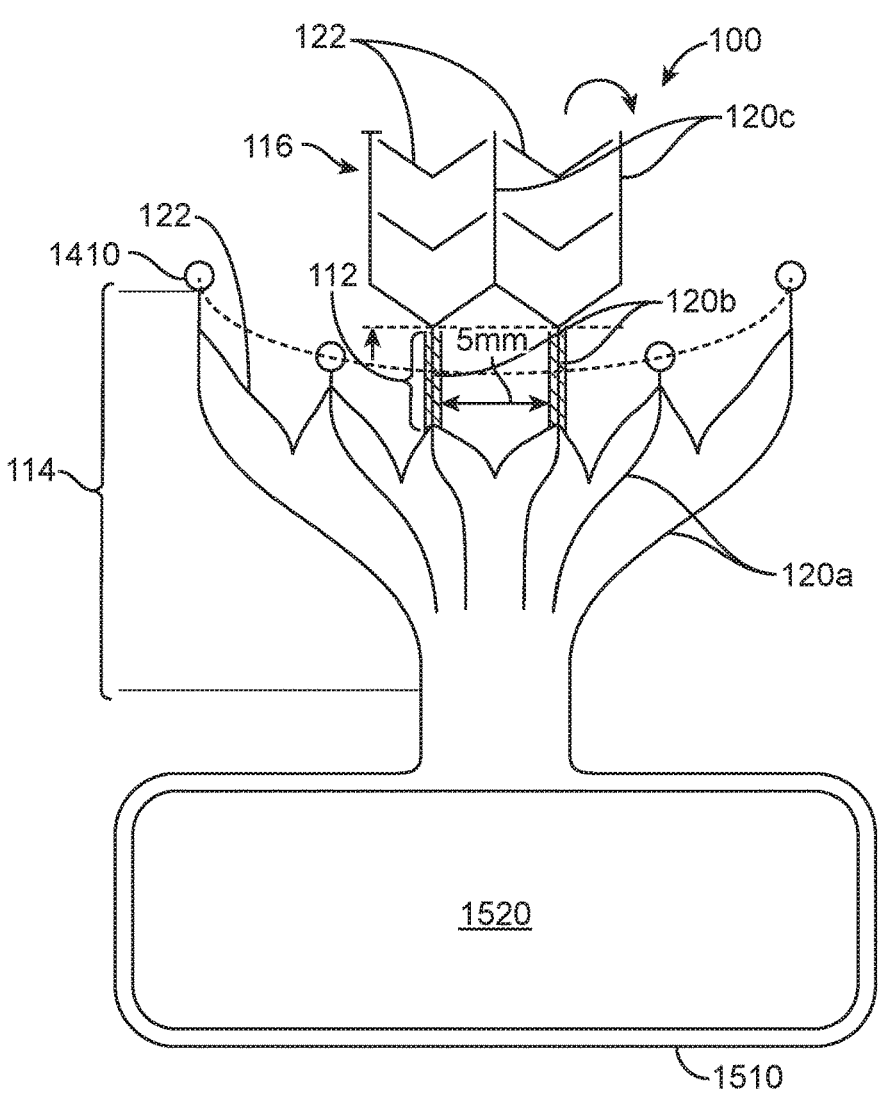
FIGS. 15A-15B depict leaflet extension devices according to the present technology.
Figure 15B:
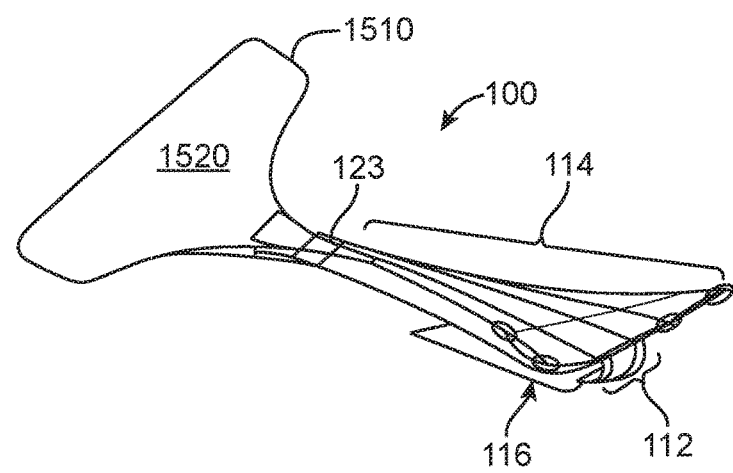

FIGS. 15A and 15B show an embodiment of a leaflet extension device 100 that can be similar to any of the devices shown and described above with reference to FIGS.

2A-14G, but the device 100 in FIGS. 15A and 15B has an atrial stabilizer 1510. The device 100 shown in FIGS. 15A and 15B can have a stabilizing portion 114 with eyelets 1410, a coaptation portion 112, and a fixation member 116. In the illustrated embodiment, the stabilizing portion 114 has first primary struts 120a, the coaptation portion 112 has second primary struts 120b that may be extendable from the first primary struts 120a, and the fixation portion 116 can have third primary struts 120c. The stabilizing portion 114 and the fixation member 116 can further include cross-struts 122. The coaptation portion 112 can slide through the eyelets 1410 to extend the coaptation portion 112 and the fixation member 116 with respect to the stabilizing portion 114 as described above with respect to FIGS. 14A-14G.

The atrial stabilizer 1510 is configured to engage the atrial wall of the heart. The atrial stabilizer 1510 is depicted as a rectangular element surrounding opening 1520, but the atrial stabilizer 1510 can be a strut or series of struts or any polygonal, circular, elliptical, oval or other shape suitable for engaging the atrial wall. In use, the atrial stabilizer 1510 is configured to contact or otherwise engage the atrial wall, and the atrial stabilizer 1510 may include frictional elements such as cleats and/or a fabric covering. The atrial stabilizer 1510 may also include a fabric covering to promote tissue ingrowth and/or encapsulation which may provide additional long-term fixation for the leaflet extension device 100.

The leaflet extension device 100 of FIGS. 15A and 15B is configured to be deployed with the stabilizing portion 114 pressing against the atrial surface of the posterior leaflet and splayed laterally and medially. Advancement of the coaptation portion 112 causes the fixation member 116 to fold against the ventricular surface of the posterior leaflet thereby clamping the device in place while simultaneously raising the coaptation portion 112 and extending the posterior leaflet towards the anterior leaflet.

The devices 100 shown and described above with respect to FIGS. 14A-15B can include additional features directed to specific functions. For example, advancing the coaptation portion 112 with respect to the stabilizing portion 114 could simultaneously deploy frictional elements, barbs, chevrons, or anchors formed with and/or on the stabilization portion 114. For example, advancing the coaptation portion 112 could drive such frictional elements down against, into, or through the atrial surface of the native leaflet. The devices 100 could also include locking elements (not illustrated) which lock the coaptation portion 112 in a specific position relative to the stabilizing portion 114. For example, the devices could have locking tabs or elements that are selectively deployed with more or less of an extension to the native leaflet. Also, the relative thickness of the stabilizing portion 114, coaptation portion 112, and fixation member 116 at each point along their length can be varied to achieve the desired range of shapes based upon the degree of deployment. In an alternative construction, the coaptation portion 112 could have separate second primary struts 120b that can be advanced individually to adjust the relative extension of the device 100 along the line of coaptation.

Figure 16:
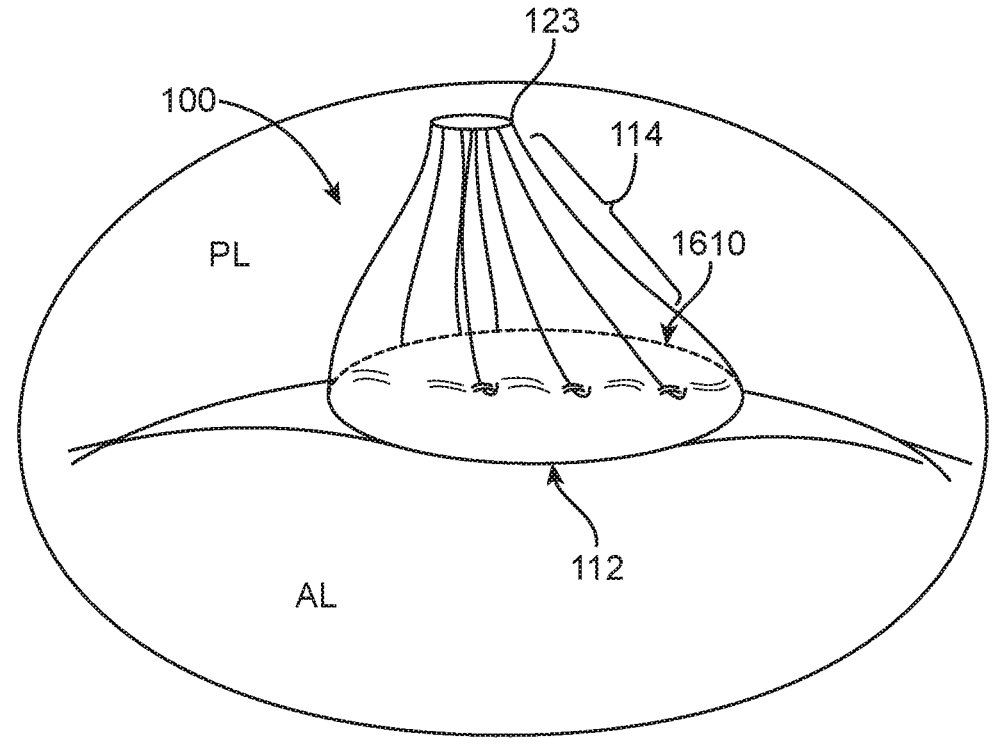
FIG. 16 illustrates a stabilizing portion of a leaflet extension device in accordance with the present technology.
Figure 17A:
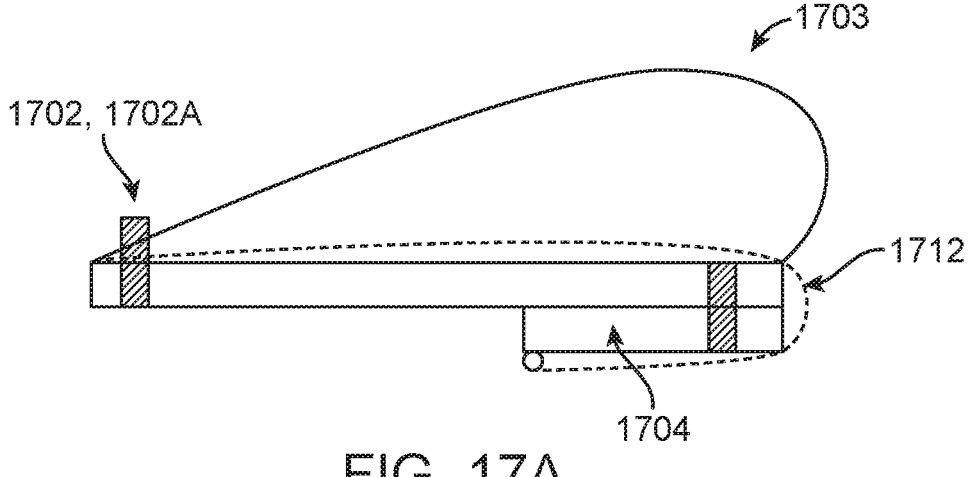
FIGS. 17A-17D illustrate additional leaflet extension devices according to the present technology.
Figure 17B:
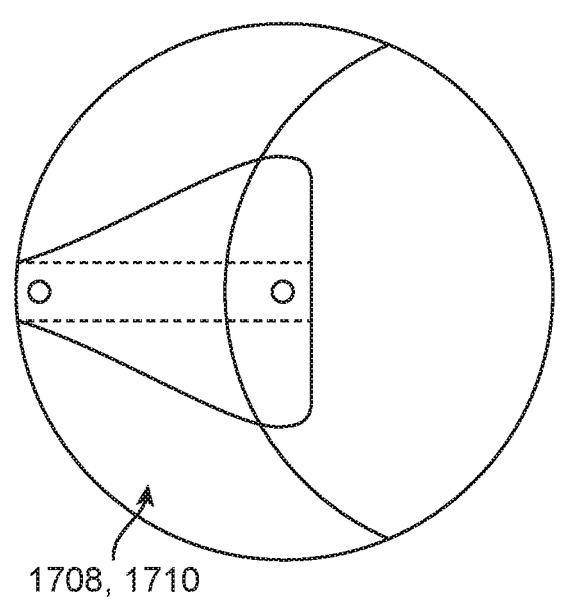
Figure 17C:
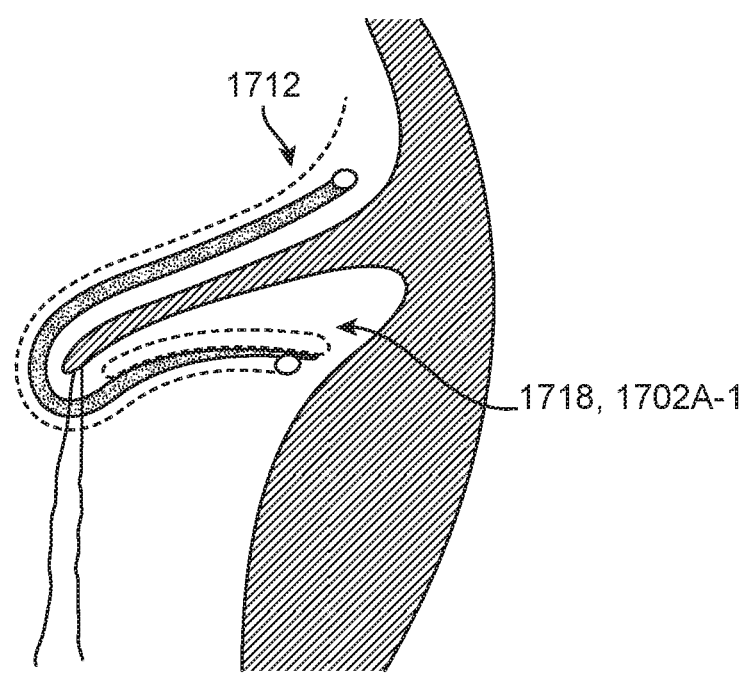
Figure 17D:
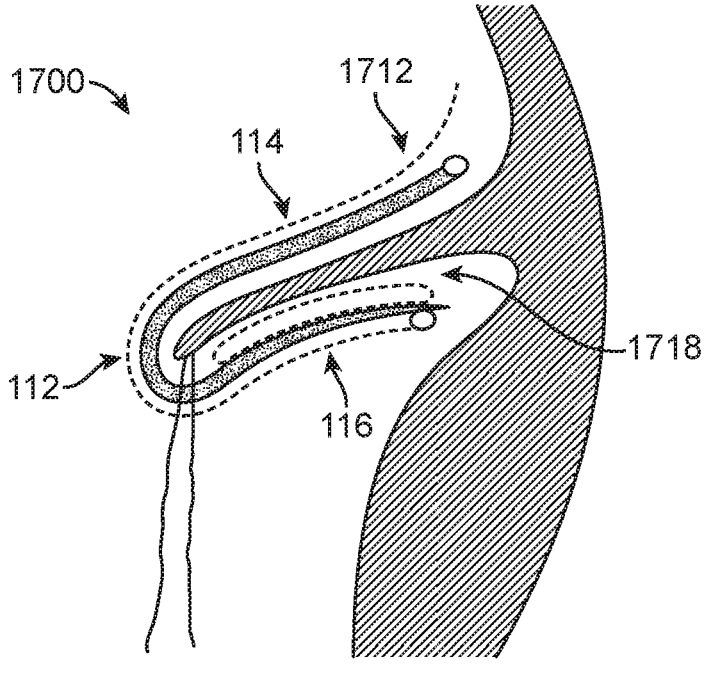

FIG. 16 shows a leaflet extension device 100 having an expandable member 110 including inflatable balloon or bladder 1610. The inflatable balloon or bladder 1610 can be used in any of the leaflet extension devices 100 described and shown above with reference to FIGS. 2A-15B either in addition to or in lieu of the frame having one or more primary struts and/or cross-struts. The inflatable bladder 1610 may be inflated once the device is in place at the native valve. The bladder 1610 may have a coaptation portion 112 configured to face the opposing leaflet such that the bladder 1610 coapts with the opposing leaflet. The bladder 1610 can be inserted into the hollow internal volume 132 (FIG. 2A) enclosed by the stabilizing portion 114 and the coaptation portion 112 shown and described above with reference to FIG. 2A. Inflating the bladder 1610 pushes the coaptation portion 112 toward the opposing cardiac valve leaflet (e.g., the anterior leaflet). The bladder 1610 can be inflated as much as needed to provide coaptation with the native anterior leaflet and eliminate regurgitation.

Leaflet Extension with Actively Displaceable Bottom Member

FIGS. 17A-17D show an example leaflet extension device 1200 which includes two members 1702, 1704. Member 1702 has a first end 1702A and an opposed second end 1702B. Member 1704 has a first end 1704A and an opposed end 1704B. The second end 1702B is attached to second end 1704B using conventional methods of attachment including screws, rivets or the like. The members 1702, 1704 may be formed of any biocompatible material including plastic, metal or the like. For example, the members 1702, 1704 may be formed of stainless steel, a nickel titanium alloy such as Nitinol®, or a Cobalt-Chromium-Nickel-Molybdenum alloy such as Elgiloy®. Members 1702 and 1704 may be formed of a solid sheet of material, a mesh, one or more struts, a lattice-work frame or the like.

Member 1702 has a first face 1702F and an opposed second face 1702G. Member 1704 has a first face 1704F and an opposed second face 1704G. The first face 1702F of the first member 1702 abuts the first face 1704F of the second member 1704. The first end 1704A of the second member 1704 is not attached to the first member 1702 and is resiliently displaceable relative to the first member 1702.

The first and second members 1702, 1704 cooperatively sandwich and grip the first native leaflet without piercing through the leaflet. The first and/or the second members may include frictional engagement members which may frictionally engage (tent into without piercing) with the native cardiac valve leaflet or the frictional engagement elements may pierce into but not through the native cardiac valve leaflet.

The leaflet extension device 1700 includes a coaptation element 1703 attached to the second face 1702G of the first member 1702. The coaptation element 1703 may have a teardrop shape and may include a convex portion 1703C extending beyond the second end 1702B, the coaptation element 1703 preferably has a smooth outer surface for atraumatically coapting with a second native leaflet (not illustrated).

The coaptation element 1703 may be formed of a biocompatible foam which may or may not include an internal framework. Alternatively, the coaptation element 1703 may be formed of a framework 1708 formed of one or more interconnected struts or a mesh. The framework 1708 encloses a hollow interior volume which is sealed by a fabric covering 1210.

A tether 1712 is operatively connected to the first and second members 1702, 1704. In some embodiments the tether 1712 is used to actively displace the second member 1204 relative to the first member 1702. The tether may be formed of a variety of biocompatible materials including a metallic wire such as stainless steel, a polymeric suture formed of expanded Polytetrafluoroethylene (ePTFE), ultra-high molecular weight polyethylene (UHMWPE), or polyester.

The first member 1702 and/or the second member 1704 may be formed of a super-elastic alloy which resiliently deforms from a native shape to a deformed shape in response to an external force but which resumes the native shape once the external force is removed, wherein pulling on the tether 1712 resiliently displaces the second member 1704 relative to the first member 1702.

An atrial stabilization member 1718 may be provided on end 1702A-1 of the first member 1702 which can be attached to wire forms that help provide atrial stabilization.

Leaflet Extension with Expandable Member

Figure 18A:
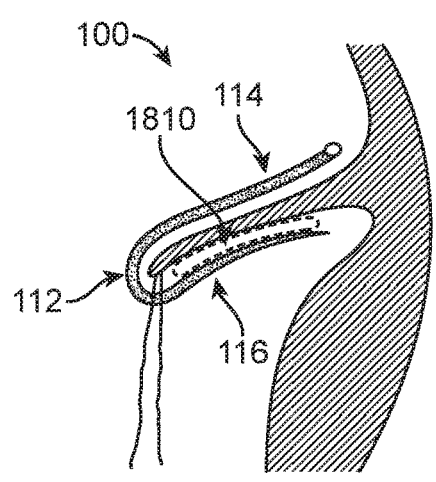
FIGS. 18A-18C illustrates leaflet extension devices with an inflatable expandable member.
Figure 18B:
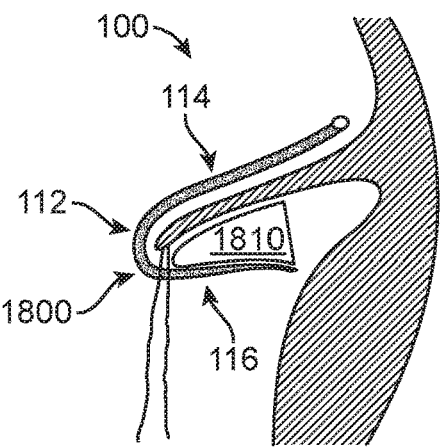
Figure 18C:
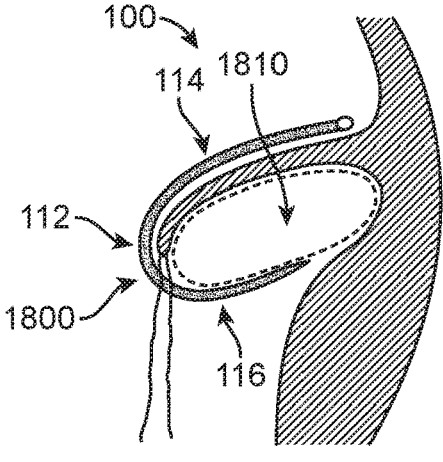

In some cases, it may be desirable to increase the effective clamping force. Adding an expandable element between the native leaflet and either the fixation member 116 or the stabilizing portion 114 may increase the effective clamping force against the leaflet and improve the fixation of the leaflet extension device 100. For example, FIGS. 18A-18C show devices that include expandable elements 1810. Although expandable elements 1810 can be placed on the atrial side of the leaflet, the present disclosure focuses on adding the expandable element 1810 between the fixation member 116 of the leaflet extension device and the ventricular surface of the native cardiac valve leaflet. Having the expandable element under the leaflet may limit motion of the device and provide a more stable structure for the opposing leaflet to close against.

For example, expandable element 1810 may also restrict the motion of the leaflet by interfering with the leaflet's ability to open fully. The expandable element 1810 may expand towards the ventricular wall, so that the expandable element touches the ventricular wall intermittently or continuously during the cardiac cycle. This may be advantageous for many reasons. It could stabilize the device 100 and/or the leaflet, reducing excessive motion and any wear, stress, or trauma on the implant, the clipped leaflet, the anterior leaflet, or adjacent leaflets.

Expandable element 1810 could potentially reduce any regurgitation in the repaired valve in a variety of ways. It could improve the ability of the leaflet extension device 100 to coapt with the opposing leaflet by pushing the leaflet extension device 100 towards the opposing leaflet. It could also improve the ability of the prosthetic device 100 to coapt with adjacent leaflets, such as the P1 and P3 cusps of the posterior leaflet, either by holding the P2 leaflet in a more appropriate position or by creating a surface against which the P1 and P3 can coapt.

FIGS. 18A-18C show examples of the expandable element 1810 in cross-section. FIG. 18A shows the device 100 when it is first placed, and FIGS. 18B and 18C after expansion of the expandable element 1810. The cross-sectional shape of the expandable member 1810 could have a variety of profiles, as shown in the differences between FIGS. 18B and 18C. For example, the native leaflet can be held in a flattened or curved shape, the expandable element 1810 can be generally round, triangular, or polygonal in cross-section, and the expandable element 1810 can extend towards the ventricular wall or not.

Figure 19:
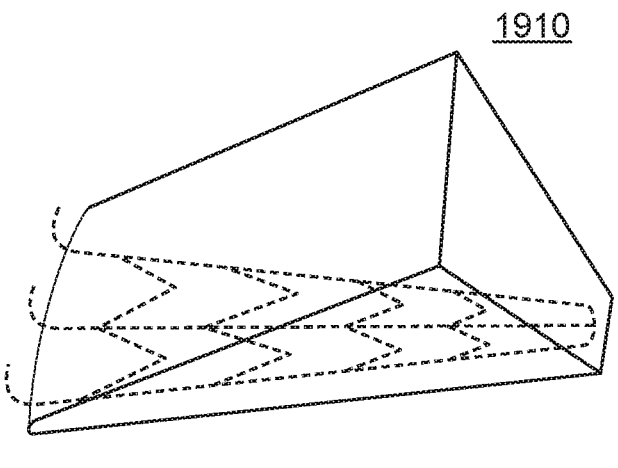
FIG. 19 illustrates an expandable member for a leaflet extension device according to the present technology.

In addition to the cross-sectional profile of the expandable element 1810, the profile of the expandable element 1810 in other dimensions is equally important. For example, the fixation member 116 might be made with a relatively narrow distal profile, to make it easier to place into the chord-free area of the posterior leaflet. When the expandable element 1810 is expanded between the fixation member 116 and the ventricular surface of the leaflet, the distal end of the expandable element 1810 may be much wider where it contacts the ventricular surface of the leaflet, as shown in FIGS. 18B and 19. This may give the expandable element 1810 a somewhat triangular profile facing the ventricular wall. Nearer the leaflet edge, the fixation member 116 may be approximately as wide as the chord-free zone of the leaflet edge, and the expandable element 1810 may be as wide or somewhat wider.

As mentioned above, the expandable element 1810 could extend posteriorly to touch or press against the ventricular wall at all times. Alternatively, it could be designed to minimize contact with the posterior wall, so that at least some range of motion remains possible for the posterior leaflet. This would allow the posterior leaflet to open somewhat in diastole, reducing any potential gradient through the mitral valve. Such a shape might also allow the leaflet and the implanted device to be pushed out of the way against the ventricular wall if it is necessary to implant a prosthetic replacement mitral valve at a later date.

Figure 20:
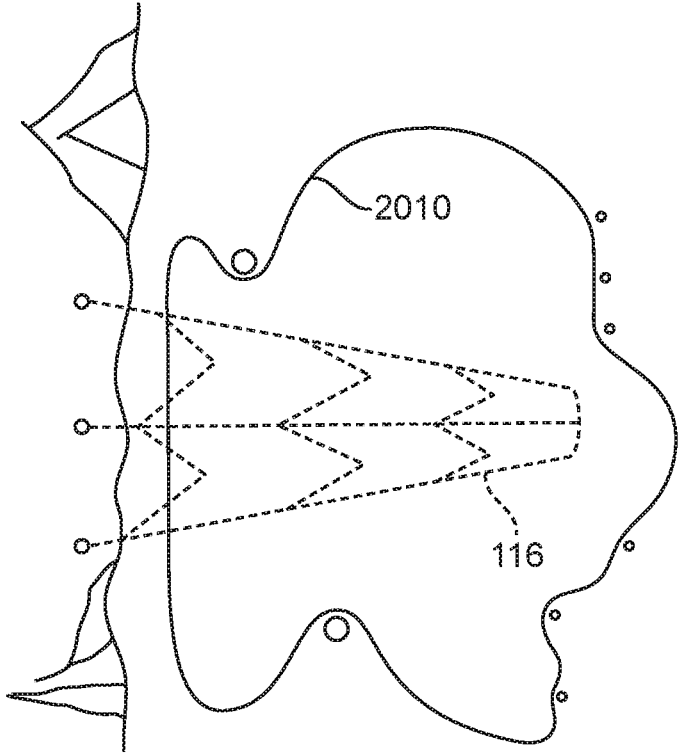
FIG. 20 illustrates an expandable member for a leaflet extension device according to the present technology.

The expandable element 1810 could also be designed to expand laterally under the ventricular side of cusps P1 and P3 of the native leaflet. Lateral expansion of the expandable member 110 could bridge any gaps between P1 and P2 or P2 and P3. They could also hold P1 and P3 in a generally closed position in alignment with the P2 leaflet. However, there may be strut chordae, tertiary chordae, or even primary chordae which might tend to interfere with the expansion of these lateral extensions. Therefore, these lateral extensions might be designed to be very low-pressure, highly expandable balloon elements which can expand around and between chordae, or they could be multiple finger-like extensions to extend between chordae, as shown in FIG. 20.

The expandable element 1810 itself could comprise an inflatable balloon or bladder. The bladder could be constructed to expand to a specific size and shape, to achieve the specific design goals outlined above. Alternatively, it could be an expandable elastic balloon, which expands in a more spherical shape until it is constrained by the rest of the device, by the chordae or valve leaflets, or by the ventricular wall.

Figure 21:
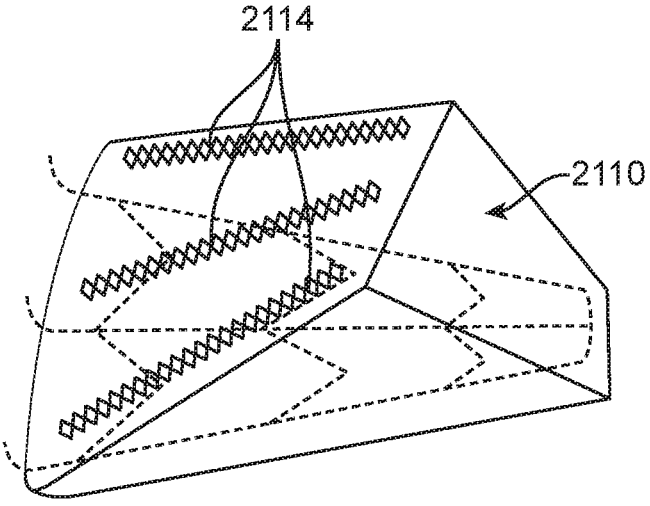
FIG. 21 depicts an enlarged view of an expandable member with frictional elements according to the present technology.

The expandable element 1810 might also have rigid or semi-rigid elements attached to it. Referring to FIG. 21, the device may include fictional elements 2114, such as bumps, spikes, or other features, which improve the frictional engagement with the valve leaflet. Alternatively, the frictional elements 2114 might be rigid or semi-rigid linear elements to constrain the expandable element 1810 into the potential shapes described above, such as a triangular, prismatic, or polyhedral shape. For example, the expandable element 1810 may have rigid linear elements affixed to the surface which apposes the ventricular surface of the leaflet to help it engage firmly with an area of the leaflet. When the expandable element 1810 is collapsed for delivery, these elements will align with the fixation member 116 to minimize the delivery profile. These rigid linear elements may also have ridges, grooves, bumps, spikes, or other features which further enhance the frictional engagement with the surface of the valve leaflet.

The expandable element 1810 can be a balloon or bladder manufactured from any biocompatible material, such as urethane, expanded PTFE, polyester, polyolefin, or other materials, or a combination thereof. For example, the bladder might have an outer surface of expanded PTFE, to optimize tissue ingrowth and the tissue compatibility of the coaptation surfaces, and an inner layer of urethane to seal the bladder for leak-free inflation.

During delivery, the expandable element 1810 might be delivered with an inflation tube inserted for inflation. This inflation tube would extend up through the delivery catheter of the device. Once the expandable element 1810 is inflated to the desired shape or volume, the tube can be withdrawn to leave the expandable element 1810 permanently inflated to that size.

The expandable element 1810 could be inflated with a polymer or polymers which cross-link or cure over a period of time, so that the size and shape of the bladder is permanent. Examples of such polymers are polyethylene glycols, silicones, methacrylates, or others. The expandable element 1810 may also be filled with coiled and/or braided structures formed of a biocompatible materials. These coils may be similar to the coils used for endovascular coiling. Alternatively, the expandable element 1810 could be inflated with saline or other biocompatible solutions which remain liquid forever. In this way, if it were desirable to deflate the expandable element 1810 in the future, for example to make room for implantation of a prosthetic mitral valve, this could be accomplished by piercing the bladder with a needle to pop it. This could be done using interventional catheter techniques.

The expandable element 1810 could alternatively be made from an elastomeric member or an expandable mechanical structure. For example, the expandable element 1810 could be an additional super-elastic frame, braid, coil, or mesh. This would allow it to be collapsed to a low profile for delivery, and then self-expand once it is in position. The braid or mesh structure can also be made out of Stainless Steel or Cobalt-Chromium-Nickel-Molybdenum alloy (e.g., Elgiloy®). Such an expandable element 1810 could have an opening allowing the internal volume to fill with blood during or after expansion.

Figure 22:
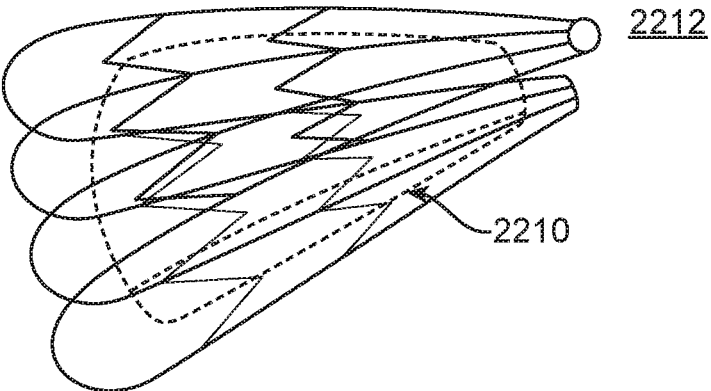
FIG. 22 depicts a leaflet extension device with an expandable member according to the present technology.

The previous embodiments have described an implantable leaflet extension device with fixation and stabilization elements formed from a super elastic Nickel-Titanium alloy (e.g. Nitinol®) frame which can be folded around the edge of the valve leaflet. As an alternative approach, this frame could be manufactured from stainless steel, cobalt-chromium steel, a "super-alloy" such as Elgiloy® which consists of 39-41% Cobalt, 19-21% Chromium, 14-16% Nickel, 11.3-20.5% Iron, 6-8% Molybdenum, and 1.5-2.5% Manganese, or other biocompatible metals or metal alloys which are stronger and stiffer than Nitinol® but do not exhibit similar super elasticity. If the leaflet extension device 1300 was made of these metals, it would have enough elasticity to fan out laterally but not enough to fold around the edge of the leaflet. Therefore, such a device with a non-super-elastic frame might be pre-formed in a u-shape so that it could be hooked under the posterior leaflet, as shown in FIG. 22. Such a device might also be formed in a "V"-shape, with a sharp edge rather than a curved edge along the edge of the extended leaflet. Such a design would not necessarily enclose a volume which would fill with blood.

The open end 2212 of the U could be formed with an opening of 3-5 mm, large enough to allow the leaflet to be hooked. Once the device was in position, an expandable element as described above could be inflated or expanded to clamp the leaflet. If the leaflet extension device 100 did not appear to adequately reduce the valve regurgitation, the device 100 could be pushed off of the posterior leaflet and retracted back into a delivery sheath. The 3-5 mm opening would be small enough that the proximal end of the hook could be captured by the open end of the sheath. This sheath would then compress the laterally expanded leaflet extension as it was advanced over the device.

The invention claimed is:

1. A device for resolving regurgitation in a cardiac valve, comprising:

an expandable member having a stabilizing portion, a fixation member in opposition to the stabilizing portion, and a coaptation portion between the stabilizing portion and the fixation member, wherein the stabilizing portion and the coaptation portion comprise a plurality of interconnected struts and together define a hollow volume, wherein the stabilizing portion and the fixation member are configured to clamp a first native leaflet of the cardiac valve between the stabilizing portion and the fixation member, and wherein the coaptation portion is configured to project from the stabilizing portion and the fixation member inwardly with respect to the first native leaflet such that the coaptation portion is positioned to at least partially coapt with a second native leaflet of the cardiac valve; and a cover attached to at least the coaptation portion of the expandable member.

2. The device of claim 1 wherein at least one of the stabilizing portion and the fixation member are formed of a super-elastic material configured to resume a native shape in the absence of a countervailing force, and wherein the stabilizing portion and the fixation member are configured to clamp the first native leaflet solely by a compressive force exerted between the stabilizing portion and the fixation member.

3. The device of claim 1, wherein the stabilizing portion comprises at least two primary struts, and each of the at least two primary struts has a first end and a second end, the first ends being commonly joined, and the second ends being splayed apart.

4. The device of claim 3, wherein the coaptation portion is configured to project inwardly with respect to a native annulus of the cardiac valve beyond a free end of the first native leaflet, and the first end of the stabilizing portion is configured to extend beyond a fixed end of the first native leaflet and superiorly along an atrial wall of the cardiac valve.

5. The device of claim 1, wherein the stabilizing portion and the fixation member clamp the first native leaflet without piercing into the first native leaflet such that the device can be repositioned and/or removed.

6. The device of claim 1, wherein the stabilizing portion comprises a lattice of the plurality of interconnected struts and openings interposed between adjacent ones of the plurality of interconnected struts.

7. The device of claim 1, wherein the fixation member comprises at least one primary strut, and the at least one primary strut is attached to the stabilizing portion.

8. The device of claim 1, wherein the fixation member comprises at least two primary struts spaced apart from one another.

9. The device of claim 8, wherein each of the at least two primary struts has a first end and a second end, the first ends are commonly joined, and the second ends are splayed apart.

10. The device of claim 1, wherein the fixation member comprises a plurality of primary struts and cross-struts between the plurality of primary struts and connected to the plurality of primary struts.

11. The device of claim 1, wherein at least one of the fixation member and the stabilizing portion further comprises frictional engagement elements.

12. The device of claim 1, wherein the cover encloses the hollow volume.

13. The device of claim 12, wherein the coaptation portion projects inwardly with respect to a native annulus beyond a free end of the first native leaflet and a first end of the stabilizing portion extends superiorly beyond a fixed end of the first native leaflet and along an atrial wall of the cardiac valve.

14. The device of claim 1 wherein the coaptation portion is integrally formed with at least one of the stabilizing portion and the fixation member.

15. The device of claim 1, wherein the coaptation portion is orthogonal to each of the stabilizing portion and the fixation member, and the coaptation portion has a concave surface configured to face the first native leaflet and a convex surface configured to face the second native leaflet.

16. The device of claim 1, further comprising an atrial stabilizer attached to a first end of the stabilizing portion, the atrial stabilizer having a polygonal shape and includes a frictional engagement element and/or a second cover.

17. The device of claim 1, further comprising an atrial stabilizer attached to a first end of the stabilizing portion, the atrial stabilizer having a polygonal shape.

18. The device of claim 1, wherein the fixation member includes at least one strut integrally formed with the coaptation portion.

19. The device of claim 1, wherein the plurality of interconnected struts define a frame at the coaptation portion.

20. The device of claim 1 wherein the coaptation portion is configured to project from the stabilizing portion and the fixation member inwardly with respect to the first native leaflet such that the coaptation portion is positioned to at least partially coapt with a plurality of leaflets of the cardiac valve including the second native leaflet.

21. A valve repair device, comprising:

an expandable member (i) comprising a frame having a plurality of interconnected struts and (ii) enclosing a hollow volume, wherein the expandable member has a first portion configured to coapt with a first native leaflet of a cardiac valve and a second portion configured to abut an atrial side of at least a portion of a second native leaflet of the cardiac valve; and a clip extending from the first portion of the expandable member, wherein the clip is configured to abut a ventricular side of at least the portion of the second native leaflet of the cardiac valve to clamp the portion of the second native leaflet between the second portion of the expandable member and the clip to secure the expandable member to the second native leaflet.

22. The valve repair device of claim 21 wherein the portion of the second native leaflet is a central portion of the second native leaflet.

23. The valve repair device of claim 21 wherein the cardiac valve is a mitral valve, wherein the second native leaflet is a posterior leaflet of the mitral valve, and wherein the portion of the posterior leaflet is at least portion of a central scallop P2 of the posterior leaflet, wherein the first native leaflet is an anterior leaflet of the mitral valve, and wherein the expandable member is sized to permit at least one lateral scallop of the posterior leaflet to coapt with the anterior leaflet.

24. The valve repair device of claim 21, further comprising a cover over the frame along at least the first portion of the expandable member, wherein the cover is configured to provide an atraumatic coaptation surface for the first native leaflet along the first portion of the expandable member.

25. The valve repair device of claim 21, further comprising a cover over at least a portion of the clip.

26. The valve repair device of claim 21, further comprising a plurality of frictional elements extending from the second portion of the expandable member, wherein the plurality of frictional elements are sized to penetrate into the atrial side of the second native leaflet without piercing completely through the second native leaflet.

27. The valve repair device of claim 21, further comprising a plurality of frictional elements extending from the clip, wherein the plurality of frictional elements are sized to penetrate into the ventricular side of the second native leaflet without piercing completely through the second native leaflet.

28. The valve repair device of claim 21 wherein the clip is separate from the expandable member and coupled to the expandable member.

29. The valve repair device of claim 21 wherein the clip is integrally formed with the expandable member.

30. The valve repair device of claim 21 wherein the clip is biased toward the second portion of the expandable member.

31. The valve repair device of claim 21 wherein the plurality of interconnected struts include a plurality of primary struts and plurality of cross struts, wherein individual ones of the plurality of cross struts extend between and connect a pair of the plurality of primary struts.

32. A valve repair device, comprising:

an expandable member (i) comprising a frame having a plurality of interconnected struts and (ii) enclosing a hollow volume, wherein the expandable member has a coaptation portion configured to coapt with a first native leaflet of a cardiac valve and a stabilizing portion configured to abut an atrial side of at least a portion of a second native leaflet of the cardiac valve; and a fixation member extending from the coaptation portion of the expandable member, wherein the fixation member is configured to abut a ventricular side of at least the portion of the second native leaflet of the cardiac valve to clamp the portion of the second native leaflet between the stabilizing portion of the expandable member and the fixation member to secure the expandable member to the second native leaflet.

33. The valve repair device of claim 32 wherein the plurality of interconnected struts include a plurality of primary struts and plurality of cross struts, wherein individual ones of the plurality of cross struts extend between and connect a pair of the plurality of primary struts.

* * * * *